(12) United States Patent
Scheller et al.

(10) Patent No.: US 9,999,436 B2
(45) Date of Patent: *Jun. 19, 2018

(54) MEMBRANE REMOVING FORCEPS

(71) Applicant: Katalyst Surgical, LLC, Chesterfield, MO (US)

(72) Inventors: Gregg D Scheller, Wildwood, MO (US); David R Chow, North York (CA)

(73) Assignee: Katalyst Surgical, LLC, Chesterfield, MO (US)

(*) Notice: Subject to any disclaimer, the term of this patent is extended or adjusted under 35 U.S.C. 154(b) by 359 days.

This patent is subject to a terminal disclaimer.

(21) Appl. No.: 14/929,595

(22) Filed: Nov. 2, 2015

(65) Prior Publication Data

US 2016/0066940 A1 Mar. 10, 2016

Related U.S. Application Data

(63) Continuation of application No. 13/797,857, filed on Mar. 12, 2013, now Pat. No. 9,204,995.

(51) Int. Cl.

| | |
|---|---|
| *A61B 17/00* | (2006.01) |
| *A61B 17/30* | (2006.01) |
| *A61F 9/007* | (2006.01) |
| *A61B 17/295* | (2006.01) |
| *A61B 17/3205* | (2006.01) |

(Continued)

(52) U.S. Cl.
CPC ............. *A61B 17/30* (2013.01); *A61B 17/29* (2013.01); *A61B 17/295* (2013.01); *A61B 17/3205* (2013.01); *A61F 9/00736* (2013.01); *A61B 2017/00349* (2013.01); *A61B 2017/00353* (2013.01); *A61B 2017/00858* (2013.01); *A61B 2017/2926* (2013.01);
(Continued)

(58) Field of Classification Search
CPC .......... A61B 17/30; A61B 2017/00349; A61B 2017/2926; A61B 2017/305; A61B 2017/320064; A61F 9/00736
See application file for complete search history.

(56) References Cited

U.S. PATENT DOCUMENTS

| | | | |
|---|---|---|---|
| 5,921,998 A | 7/1999 | Tano et al. | |
| 6,451,037 B1 * | 9/2002 | Chandrasekaran | A61B 17/320725 606/159 |

(Continued)

OTHER PUBLICATIONS

Steve Charles, Techniques and tools for dissection of epiretinal membranes, Graefe' Arch Clin Exp Ophthalmol, 241:347-352, 2003.

*Primary Examiner* — Gregory Anderson
(74) *Attorney, Agent, or Firm* — Kevin P. Rollins

(57) ABSTRACT

A membrane removing forceps may include a first forceps jaw having a first forceps jaw distal end and a first forceps jaw proximal end and a second forceps jaw having a second forceps jaw distal end and a second forceps jaw proximal end. The membrane removing forceps may include one or more abrasive surfaces configured to raise a portion of a membrane. A surgeon may raise a portion of a membrane by grazing the portion of the membrane with one or more abrasive surfaces of a membrane removing forceps. The surgeon may grasp the raised portion of the membrane with the first forceps jaw distal end and the second forceps jaw distal end. The surgeon may then remove the membrane by peeling the membrane apart from an underlying tissue.

20 Claims, 26 Drawing Sheets

(51) Int. Cl.
    *A61B 17/29*       (2006.01)
    *A61B 17/32*       (2006.01)

(52) U.S. Cl.
    CPC .................. *A61B 2017/305* (2013.01); *A61B 2017/320004* (2013.01); *A61B 2017/320064* (2013.01)

(56) References Cited

U.S. PATENT DOCUMENTS

| | | |
|---|---|---|
| 6,575,989 B1 | 6/2003 | Scheller et al. |
| 6,800,076 B2 | 10/2004 | Humayun |
| 9,204,995 B2 * | 12/2015 | Scheller .................. A61B 17/30 |
| 2007/0282348 A1 | 12/2007 | Lumpkin |
| 2008/0183199 A1 | 7/2008 | Attinger |
| 2013/0197488 A1 | 8/2013 | Scheller et al. |
| 2014/0163363 A1 | 6/2014 | Scheller et al. |
| 2014/0172010 A1 | 6/2014 | Vezzu |
| 2014/0277110 A1 | 9/2014 | Scheller et al. |
| 2015/0088193 A1 | 3/2015 | Scheller et al. |

* cited by examiner

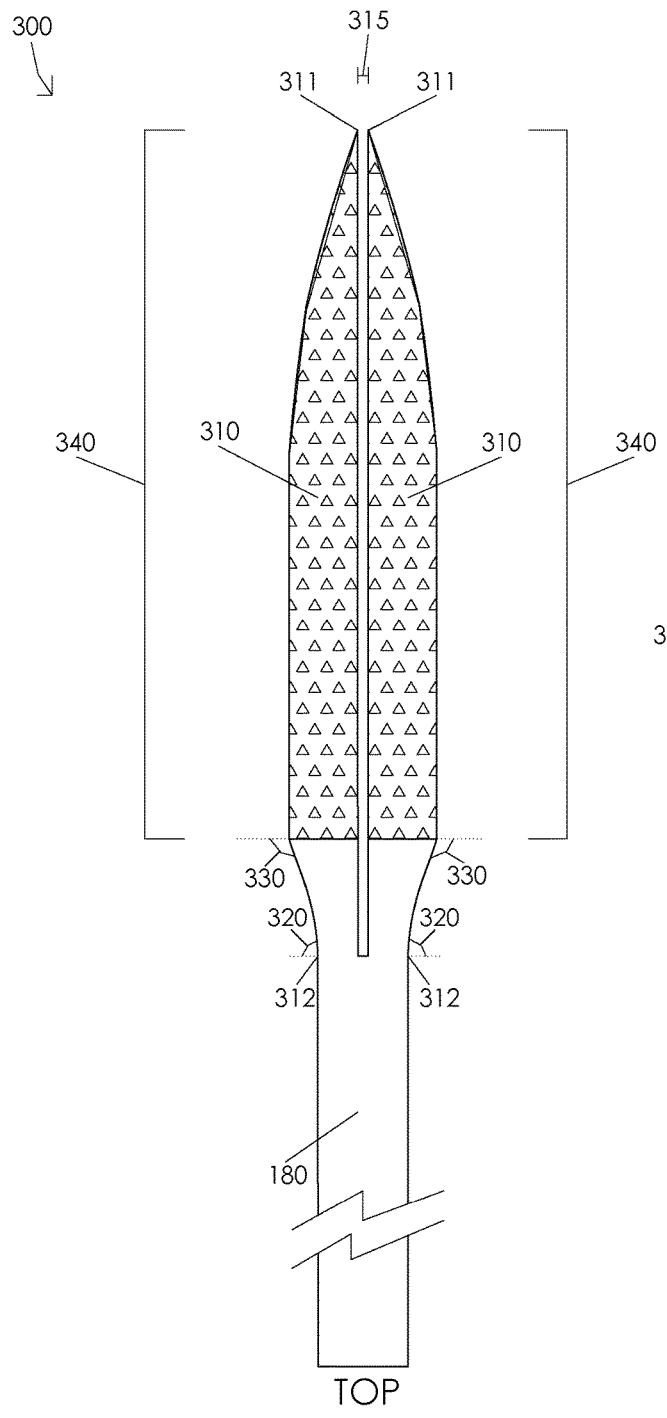
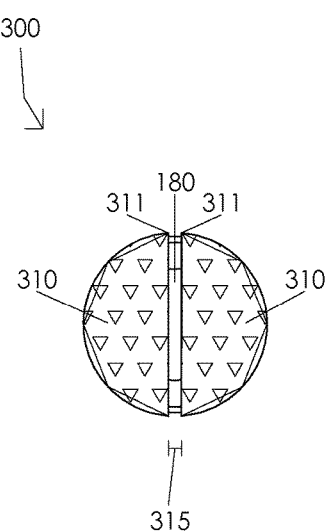
TOP
FIG. 3A
FRONT
FIG. 3B

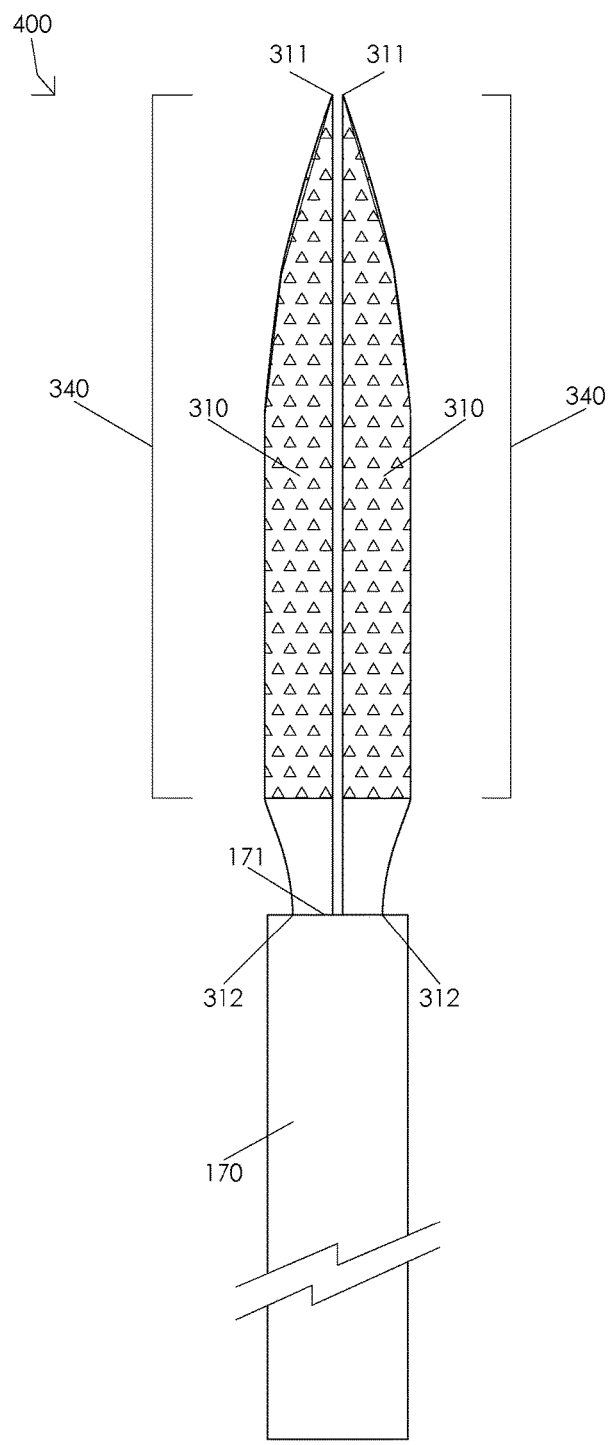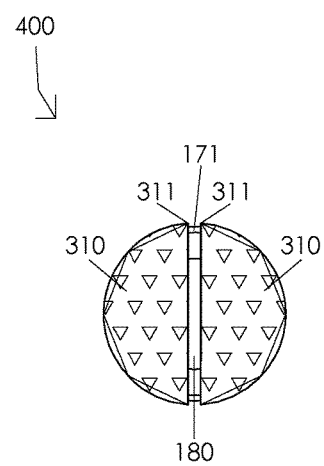
TOP
FIG. 4A
FRONT
FIG. 4B

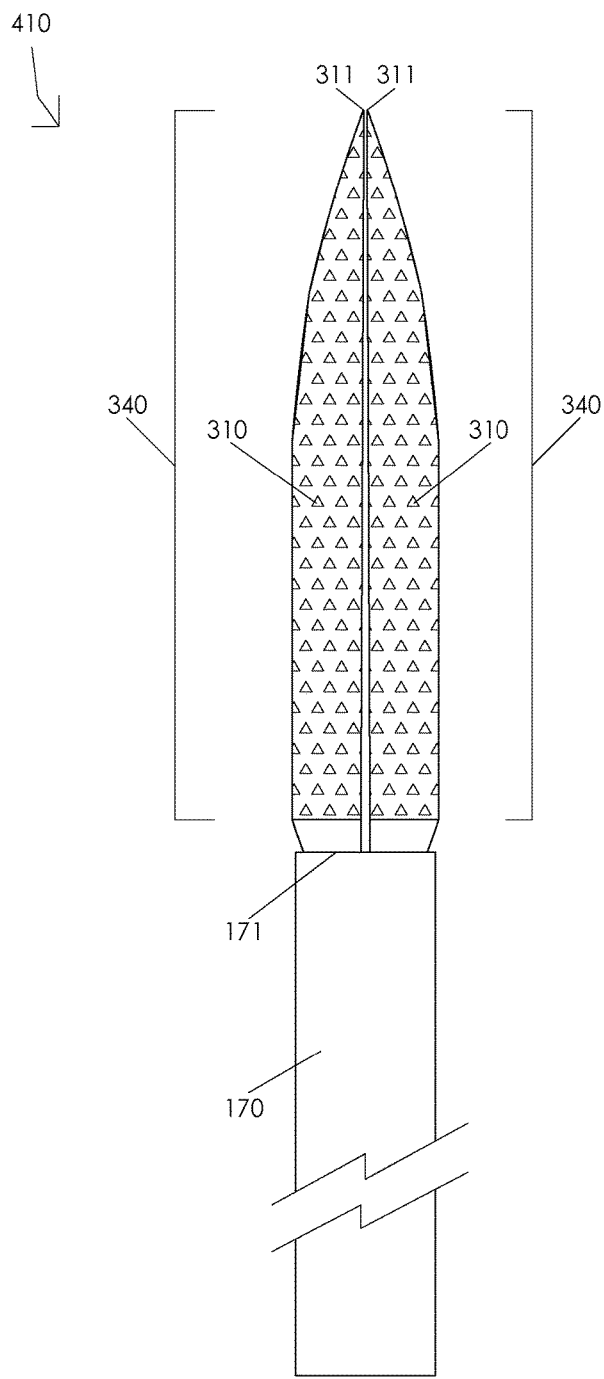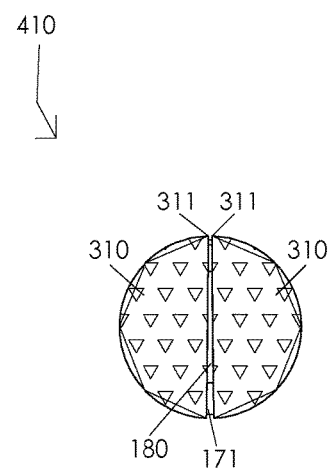
TOP
FIG. 4C
FRONT
FIG. 4D

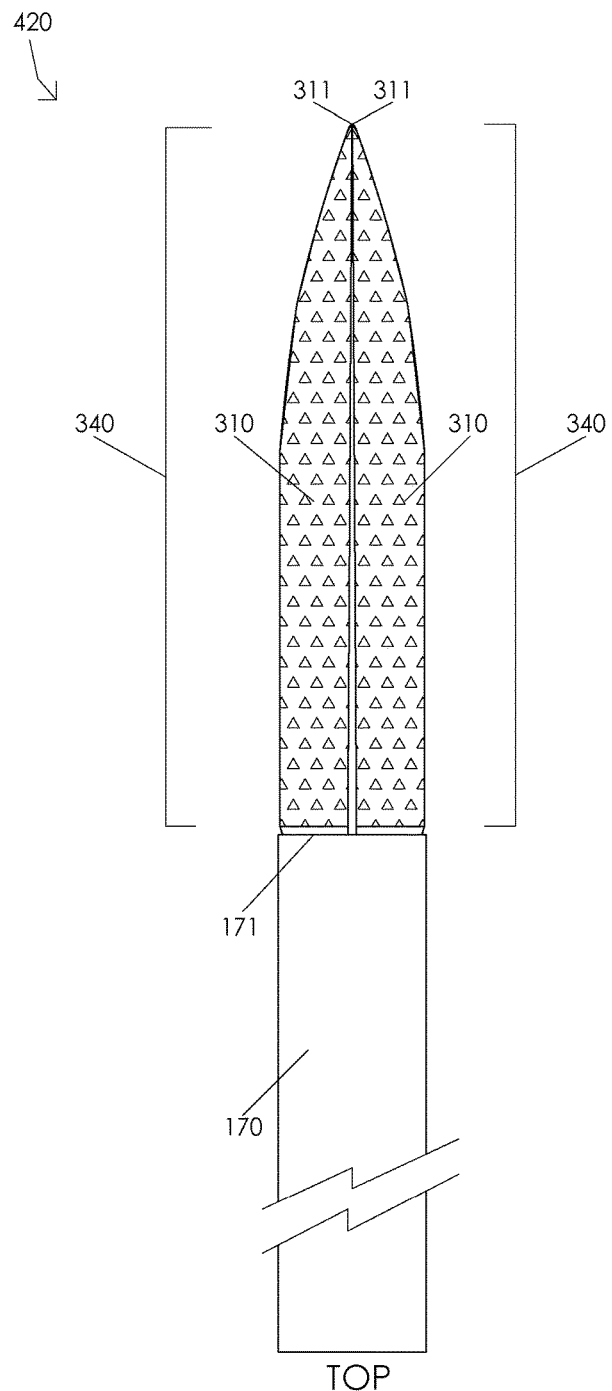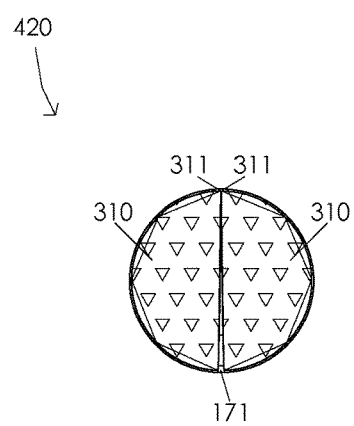
TOP
FIG. 4E
FRONT
FIG. 4F

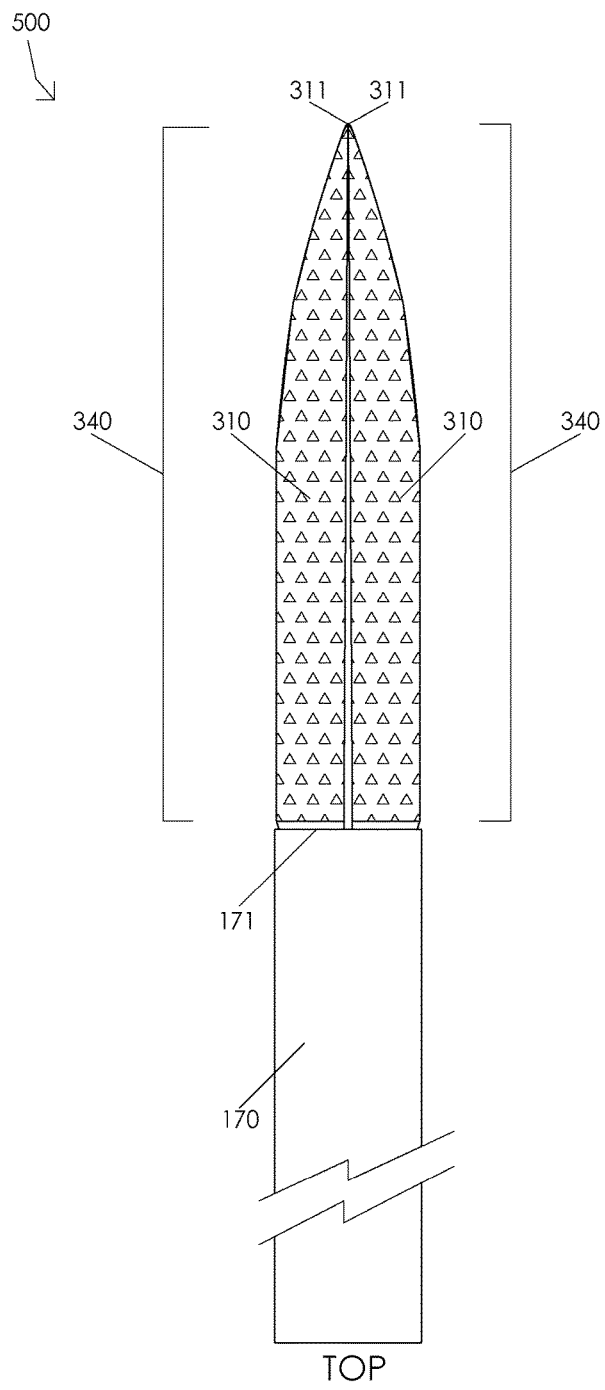
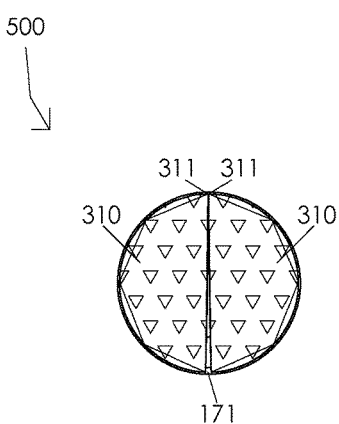
TOP
FIG. 5A
FRONT
FIG. 5B

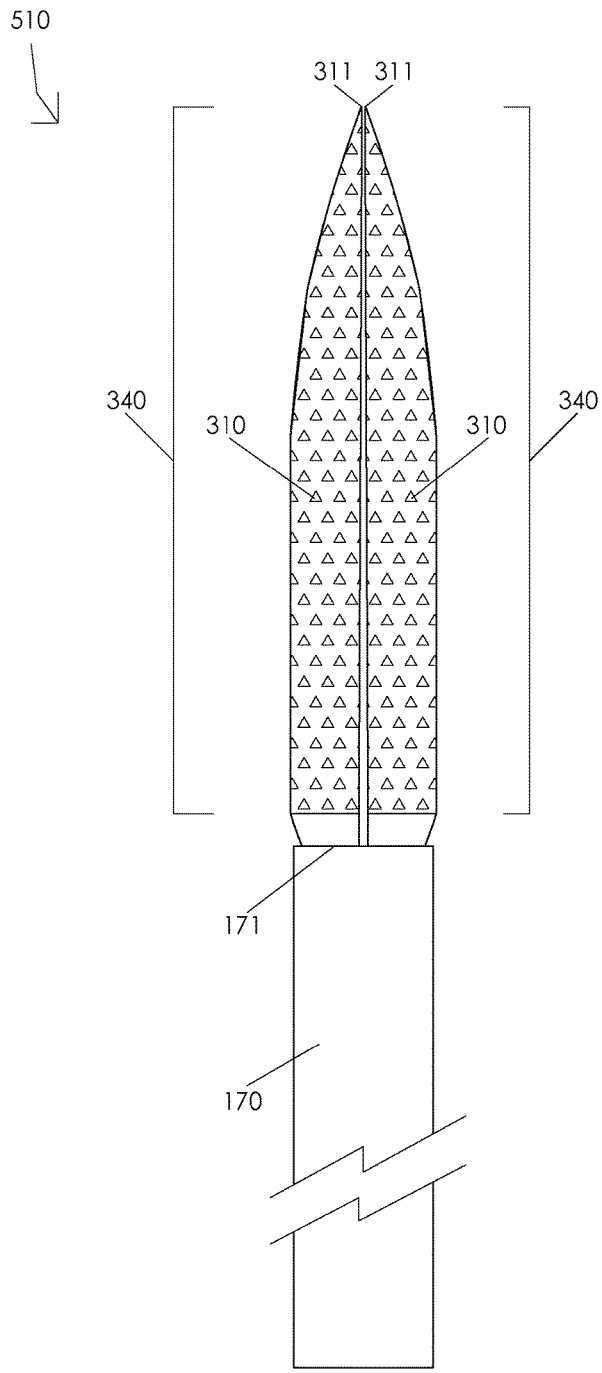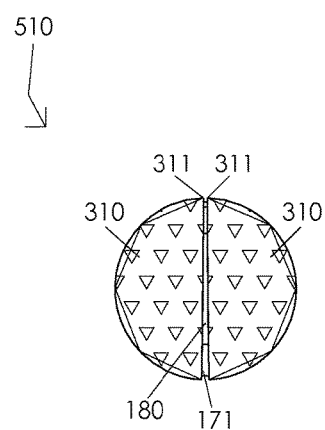
TOP
FIG. 5C
FRONT
FIG. 5D

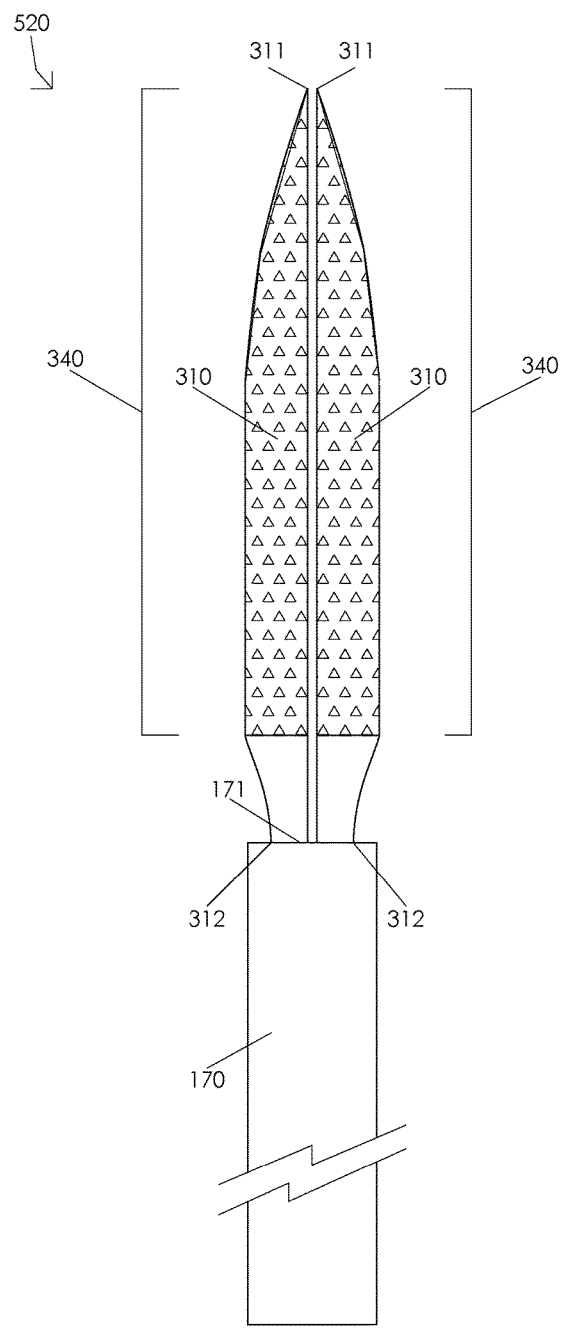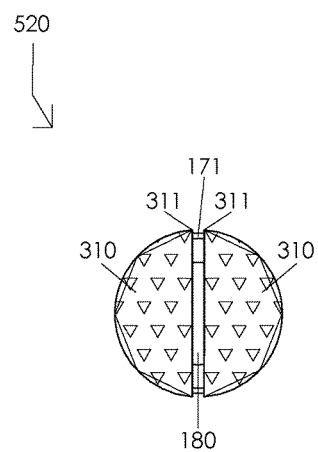
TOP
FIG. 5E
FRONT
FIG. 5F

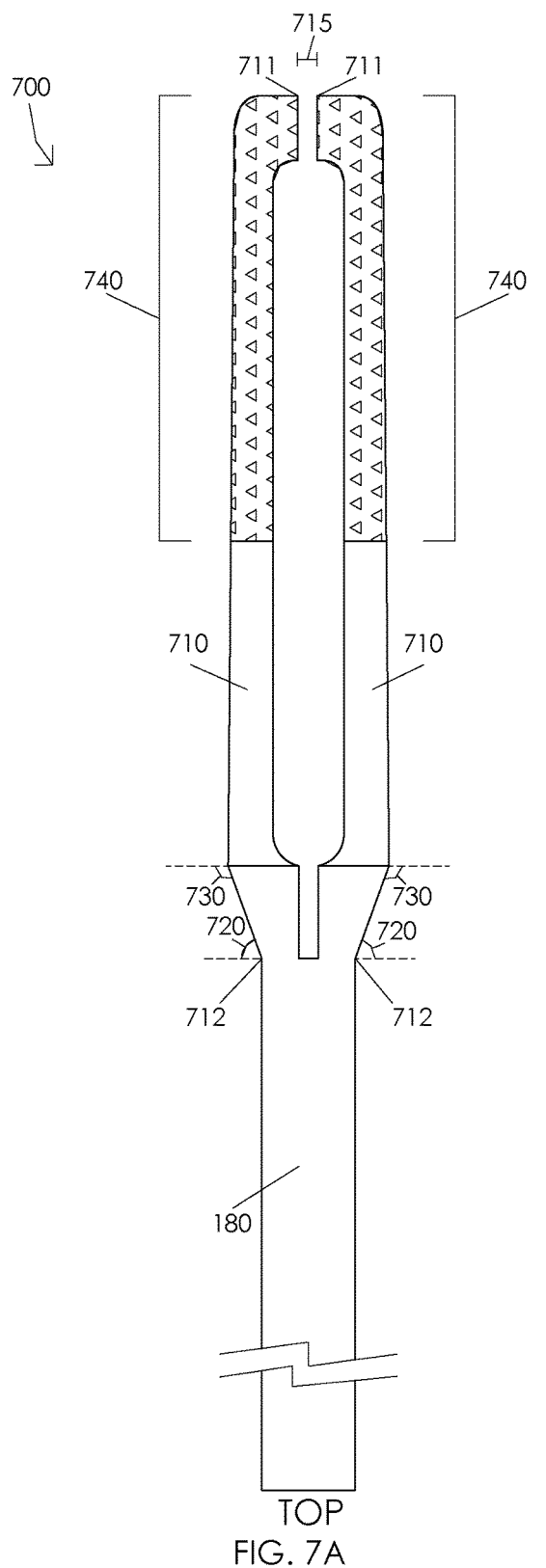
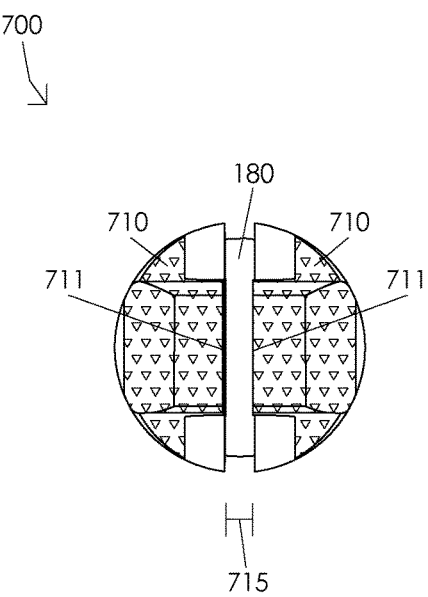
TOP
FIG. 7A
FRONT
FIG. 7B

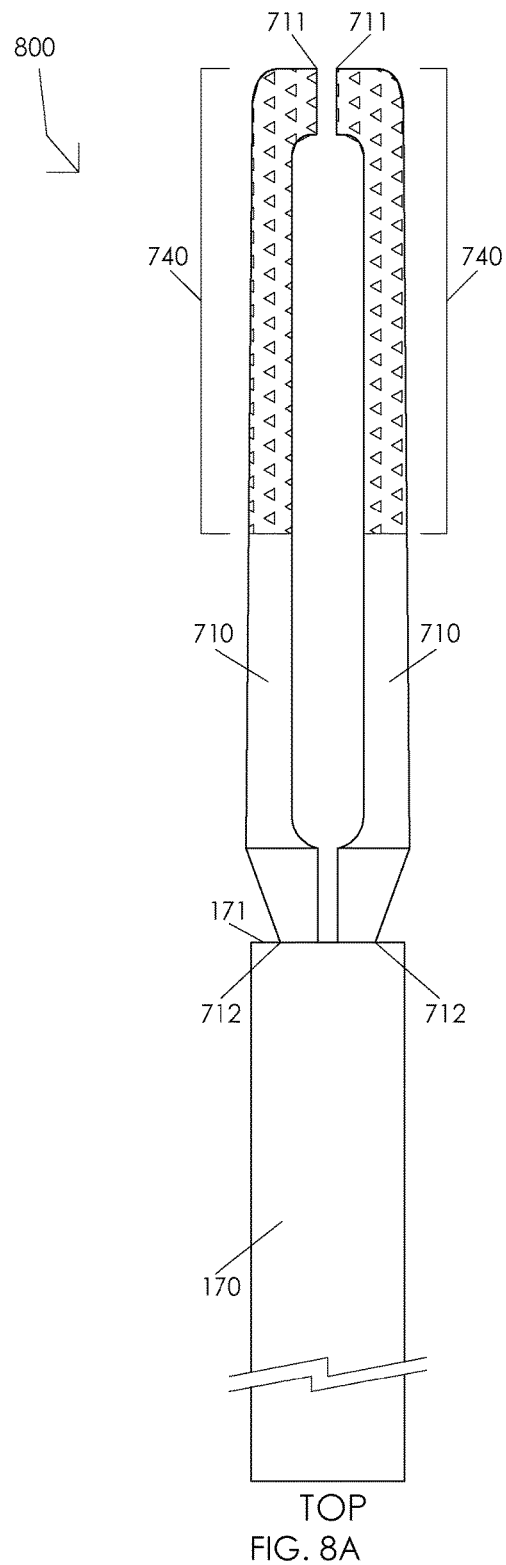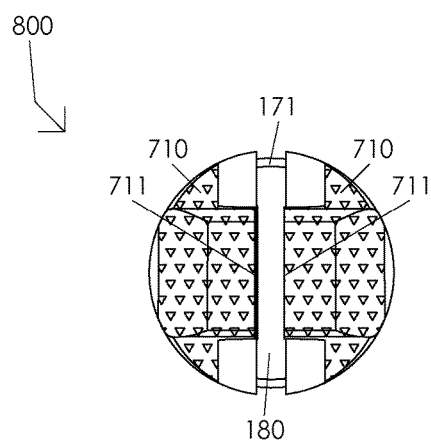
TOP
FIG. 8A
FRONT
FIG. 8B

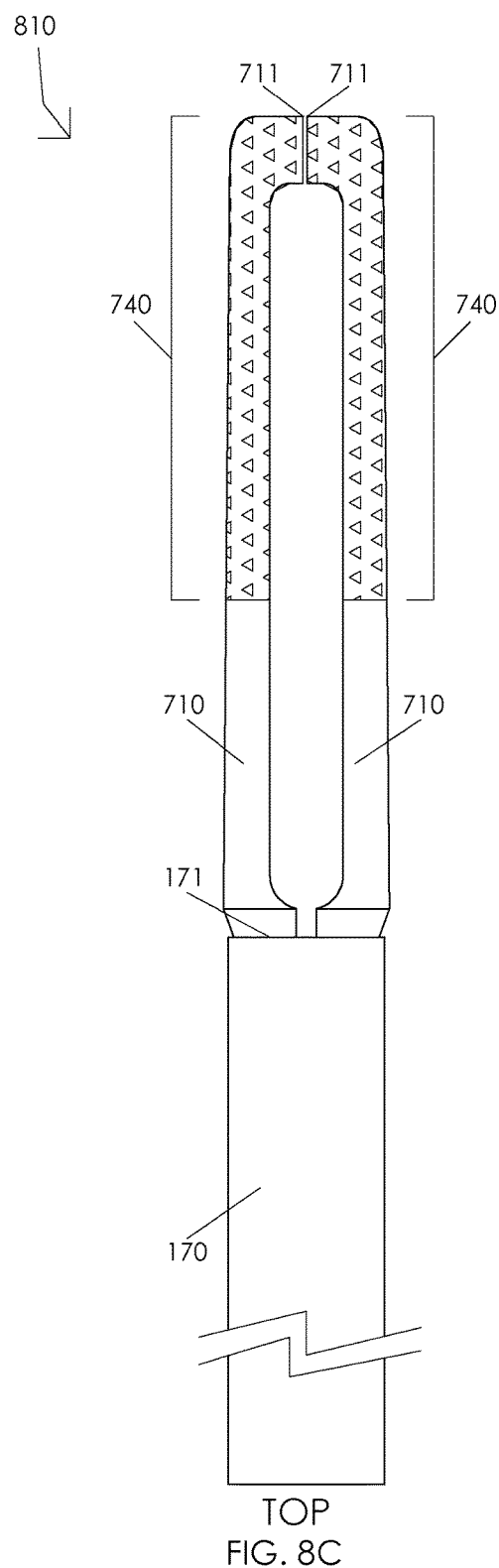
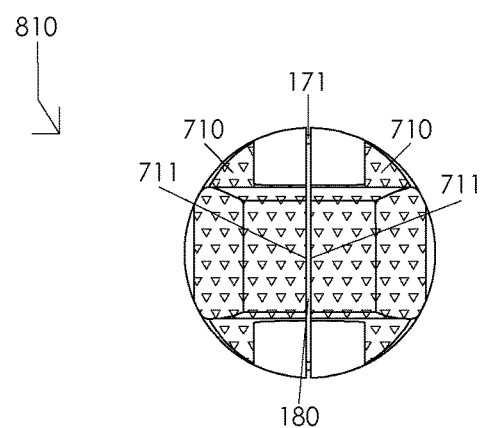
TOP
FIG. 8C
FRONT
FIG. 8D

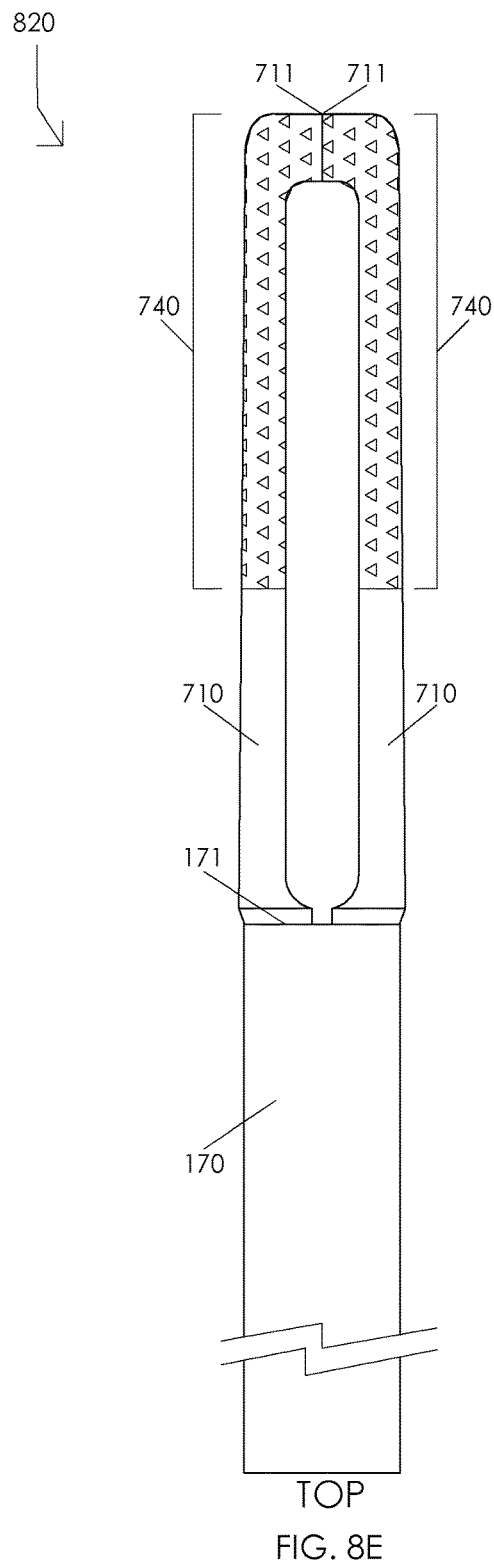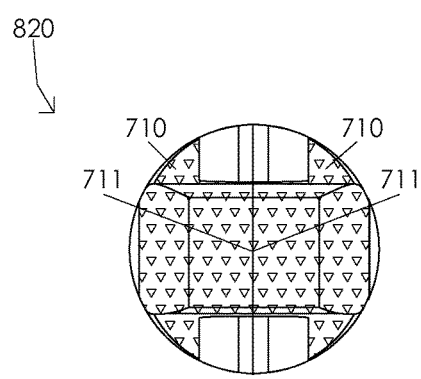
TOP
FIG. 8E
FRONT
FIG. 8F

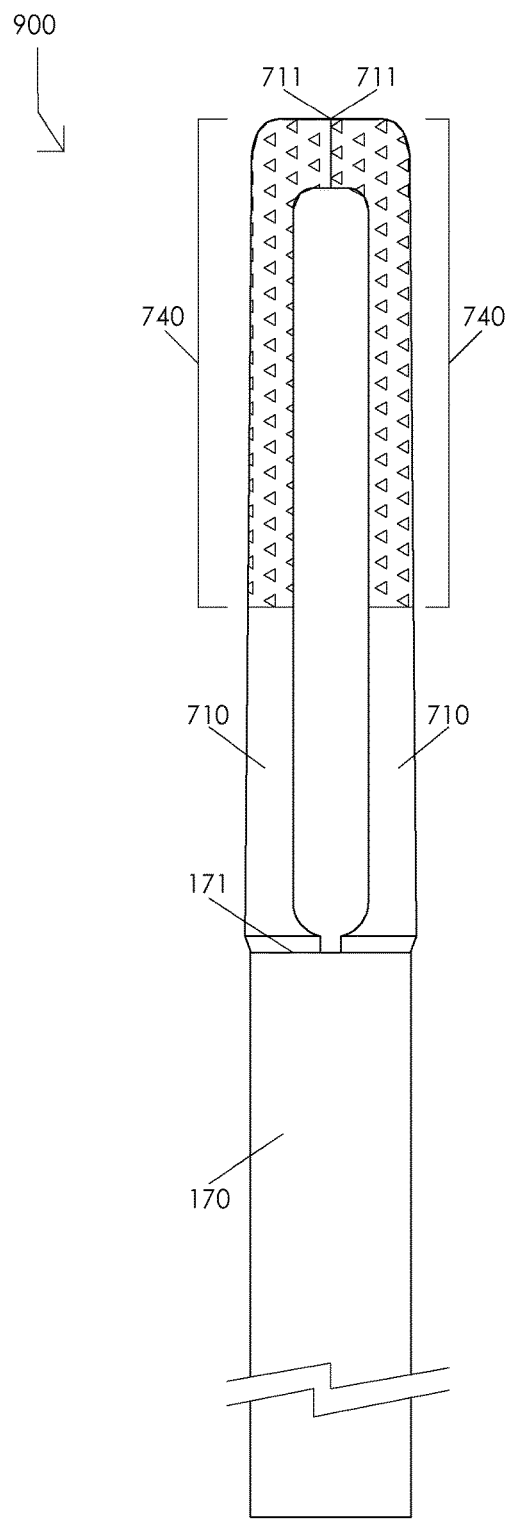
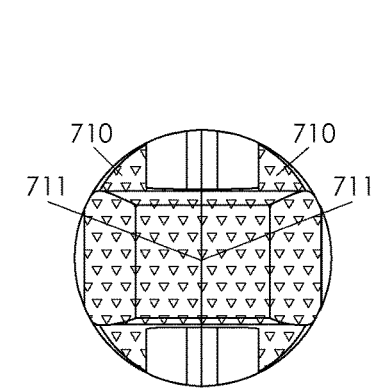
TOP
FIG. 9A
FRONT
FIG. 9B

TOP

FRONT

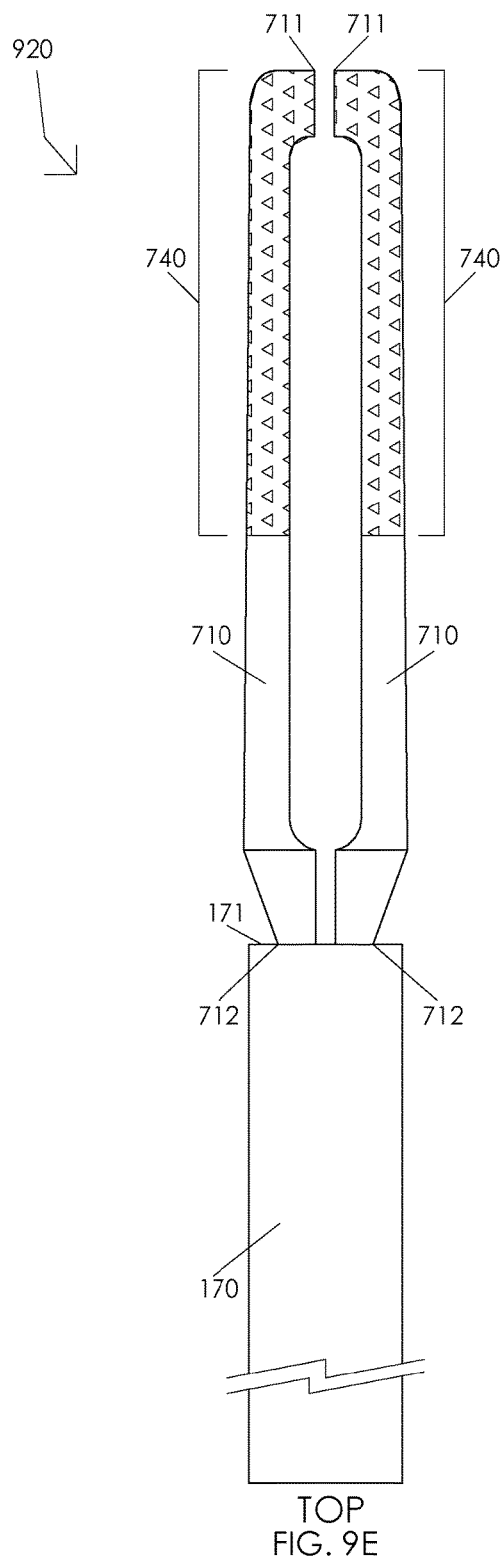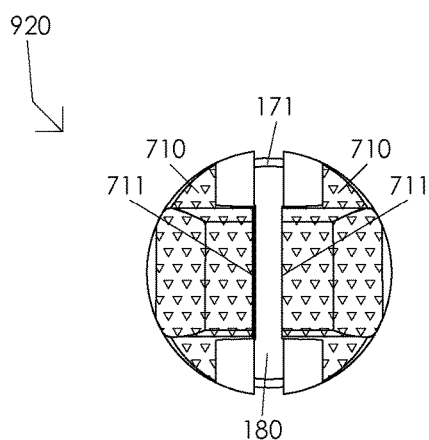
TOP
FIG. 9E
FRONT
FIG. 9F

MEMBRANE REMOVING FORCEPS

CROSS-REFERENCE TO RELATED APPLICATIONS

This application is a continuation of prior application Ser. No. 13/797,857, filed Mar. 12, 2013.

FIELD OF THE INVENTION

The present disclosure relates to a surgical instrument, and, more particularly, to a microsurgical forceps.

BACKGROUND OF THE INVENTION

A microsurgical forceps may be used to perform a microsurgical procedure, e.g., an ophthalmic surgical procedure. For example, a surgeon may use a forceps to grasp and manipulate tissues or other surgical instruments to perform portions of a surgical procedure. A particular microsurgical procedure may require a surgeon to separate a first tissue from a second tissue without causing trauma to at least one of the tissues. Such a separation procedure may be particularly difficult for a surgeon to perform if the tissue surface geometry is not flat, e.g., if the tissue surface geometry is convex. For example, an ophthalmic surgeon may be required to remove an internal limiting membrane from a patient's retina without causing trauma to the patient's retina. Accordingly, there is a need for a microsurgical forceps that enables a surgeon to separate a first tissue from a second tissue without causing significant trauma to at least one of the tissues.

BRIEF SUMMARY OF THE INVENTION

Illustratively, a membrane removing forceps may comprise a first forceps jaw having a first forceps jaw distal end and a first forceps jaw proximal end and a second forceps jaw having a second forceps jaw distal end and a second forceps jaw proximal end. In one or more embodiments, a membrane removing forceps may comprise one or more abrasive surfaces configured to raise a portion of a membrane. Illustratively, a surgeon may raise a portion of a membrane by grazing the portion of the membrane with one or more abrasive surfaces of a membrane removing forceps. In one or more embodiments, the surgeon may grasp the raised portion of the membrane with the first forceps jaw distal end and the second forceps jaw distal end. Illustratively, the surgeon may then remove the membrane by peeling the membrane apart from an underlying tissue.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 3A and 3B are schematic diagrams illustrating a membrane removing forceps;

FIGS. 4A, 4B, 4C, 4D, 4E, and 4F are schematic diagrams illustrating a gradual closing of a membrane removing forceps;

FIGS. 5A, 5B, 5C, 5D, 5E, and 5F are schematic diagrams illustrating a gradual opening of a membrane removing forceps;

FIGS. 7A and 7B are schematic diagrams illustrating a blunt-tip membrane removing forceps;

FIGS. 8A, 8B, 8C, 8D, 8E, and 8F are schematic diagrams illustrating a gradual closing of a blunt-tip membrane removing forceps;

FIGS. 9A, 9B, 9C, 9D, 9E, and 9F are schematic diagrams illustrating a gradual opening of a blunt-tip membrane removing forceps;

DETAILED DESCRIPTION OF AN ILLUSTRATIVE EMBODIMENT

Figure 1:
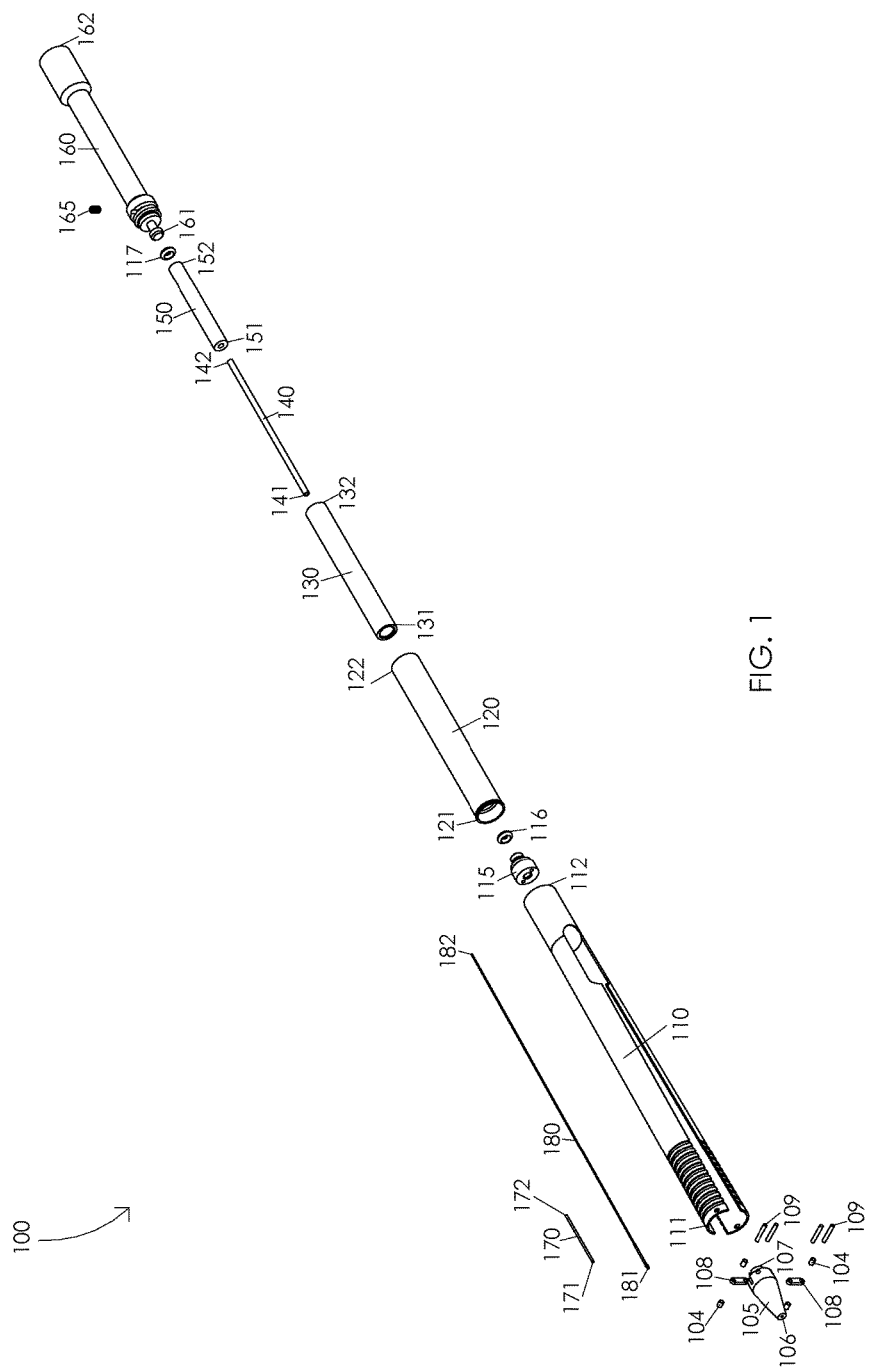
FIG. 1 is a schematic diagram illustrating an exploded view of a surgical instrument assembly.

FIG. 1 is a schematic diagram illustrating an exploded view of a surgical instrument assembly 100. In one or more embodiments, surgical instrument assembly 100 may comprise a nosecone 105 having a nosecone distal end 106 and a nosecone proximal end 107; one or more links 108; one or more link pins 109; one or more spacers 104; a handle 110 having a handle distal end 111 and a handle proximal end 112; a front plug 115; a distal O-ring 116; a proximal O-ring 117; a housing sleeve 120 having a housing sleeve distal end 121 and a housing sleeve proximal end 122; an actuation facilitating sleeve 130 having an actuation facilitating sleeve distal end 131 and an actuation facilitating sleeve proximal end 132; an inner hypodermic tube 140 having an inner hypodermic tube distal end 141 and an inner hypodermic tube proximal end 142; a piston tube 150 having a piston tube distal end 151 and a piston tube proximal end 152; an end plug 160 having an end plug distal end 161 and an end plug proximal end 162; a fixation mechanism 165; an outer hypodermic tube 170 having an outer hypodermic tube distal end 171 and an outer hypodermic tube proximal end 172; and a surgical blank 180 having a surgical blank distal end 181 and a surgical blank proximal end 182.

Illustratively, outer hypodermic tube 170 may be fixed to nosecone 105, e.g., outer hypodermic tube proximal end 172 may be fixed to nosecone distal end 106. In one or more embodiments, one or more links 108 and one or more link pins 109 may be configured to connect nosecone 105 and handle 110, e.g., a portion of nosecone 105 may be disposed within handle 110. Illustratively, nosecone 105 may be connected to one or more links 108, e.g., one or more link pins 109 may be disposed within both nosecone 105 and one or more links 108. In one or more embodiments, handle 110 may be connected to one or more links 108, e.g., one or more link pins 109 may be disposed within both handle 110 and one or more links 108. Illustratively, at least one link 108 may be connected to both nosecone 105 and handle 110, e.g., by one or more link pins 109.

In one or more embodiments, inner hypodermic tube 140 may be at least partially disposed within piston tube 150, e.g., inner hypodermic tube proximal end 142 may be disposed within piston tube 150. Illustratively, inner hypodermic tube 140 and piston tube 150 may be at least partially disposed within actuation facilitating sleeve 130. In one or more embodiments, actuation facilitating sleeve 130 and piston tube 150 may be disposed within housing sleeve 120. Illustratively, inner hypodermic tube 140 may be at least partially disposed within housing sleeve 120, e.g., inner hypodermic tube distal end 141 may extend a distance from housing sleeve distal end 121.

In one or more embodiments, distal O-ring 116 may be disposed over a portion of front plug 115. Illustratively, distal O-ring 116 may be disposed within housing sleeve 120 and actuation facilitating sleeve 130. In one or more embodiments, at least a portion of front plug 115 may be disposed within housing sleeve 120 and actuation facilitating sleeve 130, e.g., housing sleeve distal end 121 and actuation facilitating sleeve distal end 131 may be disposed over a portion of front plug 115. Illustratively, proximal O-ring 117 may be disposed over a portion of end plug 160. In one or more embodiments, proximal O-ring 117 may be disposed within housing sleeve 120 and actuation facilitating sleeve 130. Illustratively, at least a portion of end plug 160 may be disposed within housing sleeve 120 and actuation facilitating sleeve 130, e.g., housing sleeve proximal end 122 and actuation facilitating sleeve proximal end 132 may be disposed over a portion of end plug 160.

In one or more embodiments, front plug 115, distal O-ring 116, housing sleeve 120, actuation facilitating sleeve 130, piston tube 150, inner hypodermic tube 140, proximal O-ring 117, and end plug 160 may be disposed within handle 110. For example, end plug 160 may be disposed within handle 110 wherein end plug proximal end 162 may be adjacent to handle proximal end 112. Illustratively, inner hypodermic tube 140 may be fixed to nosecone 105, e.g., inner hypodermic tube distal end 141 may be fixed to nosecone proximal end 107.

In one or more embodiments, surgical blank 180 may be disposed within outer hypodermic tube 170, nosecone 105, inner hypodermic tube 140, piston tube 150, and end plug 160. Illustratively, fixation mechanism 165 may be configured to fix surgical blank 180 in a position relative to handle 110. For example, fixation mechanism 165 may comprise a setscrew configured to fix surgical blank 180 in a position relative to handle 110. In one or more embodiments, fixation mechanism 165 may comprise an adhesive material configured to fix surgical blank 180 in a position relative to handle 110. Illustratively, fixation mechanism 165 may comprise any suitable means of fixing surgical blank 180 in a position relative to handle 110.

Figure 2A:
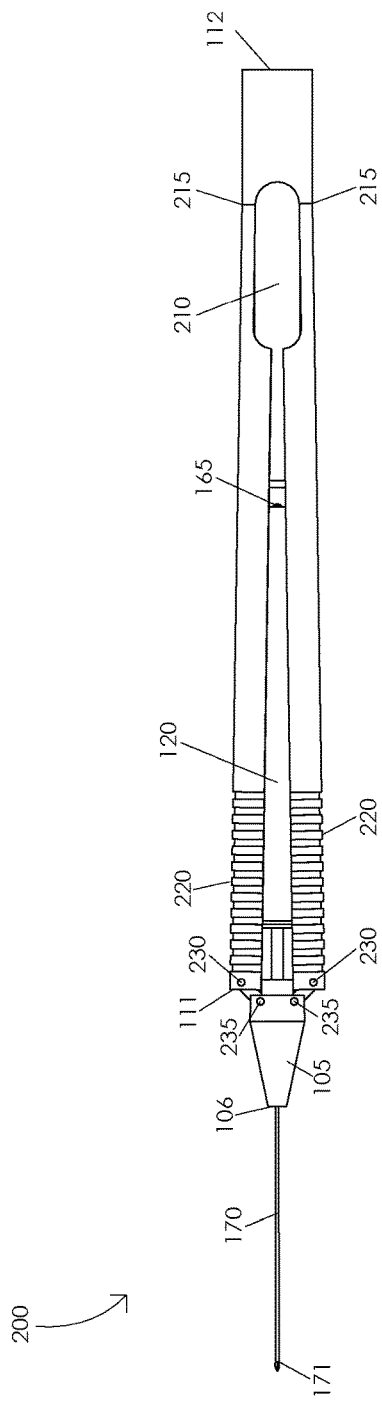
FIGS. 2A and 2B are schematic diagrams illustrating an assembled surgical instrument.
Figure 2B:
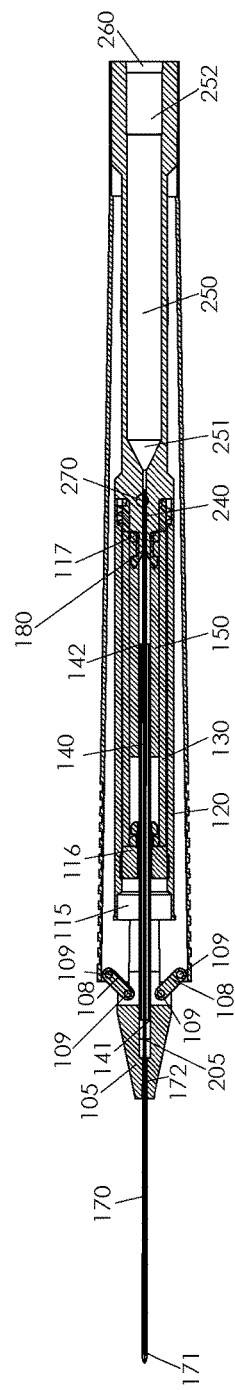

FIGS. 2A and 2B are schematic diagrams illustrating an assembled surgical instrument 200. FIG. 2A illustrates a side view of an assembled surgical instrument 200. In one or more embodiments, housing sleeve 120 may be disposed within handle 110. Illustratively, actuation facilitating sleeve 130 may be disposed within housing sleeve 120. In one or more embodiments, piston tube 150 may be disposed within actuation facilitating sleeve 130. Illustratively, a portion of inner hypodermic tube 140 may be disco posed within piston tube 150, e.g., inner hypodermic tube proximal end 142 may be disposed within piston tube 150. In one or more embodiments, a portion of inner hypodermic tube 140 may be fixed to an inner portion of piston tube 150, e.g., by a biocompatible adhesive. For example, an actuation of inner hypodermic tube 140 relative to handle 110 may be configured to actuate piston tube 150 relative to handle 110 and an actuation of piston tube 150 relative to handle 110 may be configured to actuate inner hypodermic tube 140 relative to handle 110.

Illustratively, handle 110 may comprise a spring return aperture 210. In one or more embodiments, spring return aperture 210 may comprise one or more hinges 215. Illustratively, spring return aperture 210 may be configured to separate a first portion of handle 110 and a second portion of handle 110. In one or more embodiments, spring return aperture 210 may be configured to separate a particular point on the first portion of handle 110 from a particular point on the second portion of handle 110 at a first distance. Illustratively, an application of a compressive force to a portion of handle 110 may be configured to separate the particular point on the first portion of handle 110 from the particular point on the second portion of handle 110 at a second distance. In one or more embodiments, the first distance may be greater than the second distance.

Illustratively, handle 110 may comprise one or more surgical grip points 220. In one or more embodiments, one or more surgical grip points 220 may be configured to prevent undesirable movements of handle 110, e.g., during a surgical procedure. Illustratively, one or more surgical grip points 220 may be configured to interface with a surgeon's fingertips. In one or more embodiments, one or more surgical grip points 220 may be configured to increase a total contact area between a surgeon's fingertips and handle 110. Illustratively, one or more surgical grip points 220 may be configured to facilitate an application of a compressive force to handle 110, e.g., by increasing a coefficient of friction between a surgeon's fingertips and handle 110 as the surgeon applies a compressive force to handle 110. Handle 110 may be manufactured from any suitable material, e.g., polymers, metals, metal alloys, etc., or from any combination of suitable materials.

In one or more embodiments, handle 110 may comprise one or more handle link pin housings 230. Illustratively, handle link pin housing 230 may be configured to house link pin 109. In one or more embodiments, nosecone 105 may comprise one or more nosecone link pin housings 235. Illustratively, nosecone link pin housing 235 may be configured to house link pin 109. In one or more embodiments, at least one link pin 109 may be configured to connect nosecone 105 to link 108, e.g., link pin 109 may be discs posed within both nosecone link pin housing 235 and link 108. Illustratively, at least one link pin 109 may be configured to connect handle 110 and link 108, e.g., link pin 109 may be disposed within both handle link pin housing 230 and link 108. In one or more embodiments, at least one link 108 may be connected to both nosecone 105 and handle 110, e.g., at least one link pin 109 may be disposed within both nosecone link pin housing 235 and link 108 and at least one link pin 109 may be disposed within both handle link pin housing 230 and link 108.

FIG. 2B illustrates a cross-sectional view of an assembled surgical instrument 200. In one or more embodiments, nosecone 105 may comprise a nosecone inner bore 205. Illustratively, inner hypodermic tube distal end 141 may be fixed within nosecone inner bore 205, e.g., by a machine press fit, a biocompatible adhesive, etc. In one or more embodiments, outer nosecone proximal end 172 may be fixed within nosecone inner bore 205, e.g., by a machine press fit, a biocompatible adhesive, etc.

Illustratively, end plug 160 may comprise a surgical blank housing 240, an end plug inner bore 250, an interface taper 260, and a fixation mechanism housing 270. In one or more embodiments, end plug inner bore 250 may comprise an end plug inner bore distal cone 251 and an end plug inner bore proximal chamber 252. Illustratively, interface taper 260 may be configured to interface with one or more components, e.g., to provide one or more surgical utilities. In one or more embodiments, interface taper 260 may comprise a Luer taper. End plug 160 may be manufactured from any suitable material, e.g., polymers, metals, metal alloys, etc., or from any combination of suitable materials.

Illustratively, surgical blank 180 may be disposed within outer hypodermic tube 170, nosecone inner bore 205, inner hypodermic tube 140, piston tube 150, actuation facilitating sleeve 130, surgical blank housing 240, and fixation mechanism housing 270. In one or more embodiments, fixation mechanism 165 may be configured to fix surgical blank 180 in a position relative to handle 110, e.g., at fixation mechanism housing 270. For example, fixation mechanism 165 may be disposed within fixation mechanism housing 270, e.g., to fix surgical blank 180 in a position relative to handle 110.

Illustratively, surgical blank 180 may modified to provide a one or more surgical utilities, e.g., surgical blank distal end 181 may be modified to provide one or more particular surgical utilities of a plurality of surgical utilities. In one or more embodiments, surgical blank 180 may be modified wherein surgical blank 180 may comprise a surgical forceps, e.g., with a grasping utility. Illustratively, surgical blank 180 may be modified wherein surgical blank 180 may comprise a surgical scissors, e.g., with a cutting utility. In one or more embodiments, surgical blank 180 may be modified wherein surgical blank 180 may comprise a surgical manipulator, e.g., with a manipulation utility. Illustratively, surgical blank 180 may be modified wherein surgical blank 180 may comprise a surgical hook, e.g., with a hook utility. In one or more embodiments, surgical blank 180 may be modified wherein surgical blank 180 may comprise a surgical chopper, e.g. with a chopping utility. Illustratively, surgical blank 180 may be modified wherein surgical blank 180 may comprise a surgical pre-chopper, e.g., with a pre-chopping utility. In one or more embodiments, surgical blank 180 may be modified wherein surgical blank 180 may comprise a surgical pick, e.g., with a pick utility. Illustratively, surgical blank 180 may be modified to comprise any surgical instrument with any surgical utility as will be appreciated by one having ordinary skill in the relevant technological art. Surgical blank 180 may be manufactured from any suitable material, e.g., polymers, metals, metal alloys, etc., or from any combination of suitable materials.

In one or more embodiments, handle 110 may be compressed, e.g., by an application of a compressive force to handle 110. For example, a surgeon may compress handle 110 by gently squeezing handle 110, e.g., at one or more surgical grip points 220. Illustratively, a compression of handle 110 may be configured to actuate nosecone 105 relative to handle proximal end 112. Illustratively, a compression of handle 110 may be configured to extend nosecone 105 relative to handle proximal end 112.

In one or more embodiments, a compression of handle 110 may be configured to extend one or more links 108 connected to nosecone 105, e.g., by one or more link pins 109, away from handle proximal end 112. Illustratively, a compression of handle 110 may be configured to gradually project nosecone 105 relative to handle proximal end 112. In one or more embodiments, a compression of handle 110 may be configured to gradually actuate outer hypodermic tube 170 relative to handle proximal end 112. For example, a compression of handle 110 may be configured to gradually extend outer hypodermic tube 170 relative to handle proximal end 112. Illustratively, a compression of handle 110 may be configured to gradually actuate outer hypodermic tube 170 relative to surgical blank 180. For example, a compression of handle 110 may be configured to gradually extend outer hypodermic tube 170 relative to surgical blank 180.

In one or more embodiments, a compression of handle 110 may be configured to actuate inner hypodermic tube 140 relative to handle 110. Illustratively, a compression of handle 110 may be configured to extend inner hypodermic tube 140 relative to handle proximal end 112. In one or more embodiments, a compression of handle 110 may be configured to actuate piston tube 150 relative to handle 110. Illustratively, a compression of handle 110 may be configured to extend piston tube 150 relative to handle proximal end 112.

In one or more embodiments, handle 110 may be decompressed, e.g., by reducing a magnitude of a compressive force applied to handle 110. For example, a surgeon may decompress handle 110 by decreasing an amount of compressive force applied to handle 110, e.g., at one or more surgical grip points 220. Illustratively, a decompression of handle 110 may be configured to actuate nosecone 105 relative to handle proximal end 112. Illustratively, a decompression of handle 110 may be configured to retract nosecone 105 relative to handle proximal end 112.

In one or more embodiments, a decompression of handle 110 may be configured to retract one or more links 108 connected to nosecone 105, e.g., by one or more link pins 109, towards handle proximal end 112. Illustratively, a decompression of handle 110 may be configured to gradually retract nosecone 105 relative to handle proximal end 112. In one or more embodiments, a decompression of handle 110 may be configured to gradually actuate outer hypodermic tube 170 relative to handle proximal end 112. For example, a decompression of handle 110 may be configured to gradually retract outer hypodermic tube 170 relative to handle proximal end 112. Illustratively, a decompression of handle 110 may be configured to gradually actuate outer hypodermic tube 170 relative to surgical blank 180. For example, a decompression of handle 110 may be configured to gradually retract outer hypodermic tube 170 relative to surgical blank 180.

In one or more embodiments, a decompression of handle 110 may be configured to actuate inner hypodermic tube 140 relative to handle 110. Illustratively, a decompression of handle 110 may be configured to retract inner hypodermic tube 140 relative to handle proximal end 112. In one or more embodiments, a decompression of handle 110 may be configured to actuate piston tube 150 relative to handle 110. Illustratively, a decompression of handle 110 may be configured to retract piston tube 150 relative to handle proximal end 112.

In one or more embodiments, actuation facilitating sleeve 130 and piston tube 150 may be configured to minimize a coefficient of friction between actuation facilitating sleeve 130 and piston tube 150. Illustratively, actuation facilitating sleeve 130 and piston tube 150 may be manufactured from one or more materials configured to minimize a friction force, e.g., when piston tube 150 is actuated relative to handle 110. For example, actuation facilitation sleeve 130 and piston tube 150 may be manufactured from one or more materials configured to minimize a friction force, e.g., when piston tube 150 is actuated relative to actuation facilitating sleeve 130. In one or more embodiments, at least an inner portion of actuation facilitating sleeve 130 may comprise a non-crystalline material, e.g., glass. Illustratively, at least an outer portion of piston tube 150 may comprise carbon or a carbon allotrope, e.g., graphite. In one or more embodiments, at least an inner portion of actuation facilitating sleeve 130 may comprise a carbon or a carbon allotrope, e.g., graphite. Illustratively, at least an outer portion of piston tube 150 may comprise a non-crystalline material, e.g., glass.

Actuation facilitating sleeve 130 may be manufactured from any suitable material, e.g., polymers, metals, metal alloys, etc., or from any combination of suitable materials. Piston tube 150 may be manufactured from any suitable material, e.g., polymers, metals, metal alloys, etc., or from any combination of suitable materials. In one or more embodiments, an inner portion of actuation facilitating sleeve 130 may be coated with a material configured to minimize a coefficient of friction between actuation facilitating sleeve 130 and piston tube 150, e.g., Teflon. Illustratively, an outer portion of piston tube 150 may be coated with a material configured to minimize a coefficient of friction between piston tube 150 and actuation facilitation sleeve 130, e.g., Teflon.

FIGS. 3A and 3B are schematic diagrams illustrating a membrane removing forceps 300. FIG. 3A illustrates a top view and FIG. 3B illustrates a front view of a membrane removing forceps 300. Illustratively, membrane removing forceps 300 may be manufactured with dimensions configured for performing microsurgical procedures, e.g., ophthalmic surgical procedures. In one or more embodiments, membrane removing forceps 300 may be manufactured from surgical blank 180. Illustratively, membrane removing forceps 300 may be manufactured by modifying surgical blank 180, e.g., with an electric discharge machine. In one or more embodiments, membrane removing forceps 300 may be manufactured by modifying surgical blank 180, e.g., with a laser, a file, or any suitable modification means. Illustratively, membrane removing forceps 300 may comprise a plurality of forceps jaws 310, a first contour angle 320, a second contour angle 330, and one or more abrasive surfaces 340.

In one or more embodiments, abrasive surface 340 may be configured to grasp a portion of a membrane, e.g., abrasive surface 340 may be configured to grasp a portion of an internal limiting membrane 650. Illustratively, a surgeon may maneuver a portion of abrasive surface 340 across a portion of a membrane, e.g., to raise a portion of the membrane. In one or more embodiments, abrasive surface 340 may be configured to grasp a portion of a first tissue disposed over a second tissue without damaging the second tissue. Illustratively, abrasive surface 340 may be configured to grasp a first tissue having a convex surface geometry disposed over a second tissue having a convex surface geometry without damaging the second tissue.

In one or more embodiments, abrasive surface 340 may be manufactured by fixing particles, e.g., inert particles, to a portion of membrane removing forceps 300. Illustratively, particles may be fixed to a portion of membrane removing forceps 300, e.g., by an adhesive or any suitable fixation means. In one or more embodiments, particles may be fixed to a portion of membrane removing forceps 300 by a biocompatible high temperature epoxy. Illustratively, particles may be fixed to a portion of membrane removing forceps 300 by a biocompatible spectrally transparent epoxy. In one or more embodiments, a portion of membrane removing forceps 300 may be coated by a material configured to facilitate adhesion of particles. Illustratively, a portion of membrane removing forceps 300 may be coated by a material, e.g., silicon, and then particles may be fixed to the material, e.g., by an adhesive or any suitable fixation means.

In one or more embodiments, abrasive surface 340 may be manufactured by fixing particles to a portion of membrane removing forceps 300, e.g., particles may comprise diamond particles, sapphire particles, ruby particles, emerald particles, etc. Illustratively, abrasive surface 340 may be manufactured by fixing biocompatible particles to a portion of membrane removing forceps 300. In one or more embodiments, abrasive surface 340 may be manufactured by fixing particles having particle diameters in a range of 5.0 to 25.0 micrometers to a portion of membrane removing forceps 300, e.g., abrasive surface 340 may be manufactured by fixing particles having particle diameters of 15.0 micrometers to a portion of membrane removing forceps 300. Illustratively, abrasive surface 340 may be manufactured by fixing particles having particle diameters less than 5.0 micrometers or greater than 25.0 micrometers to a portion of membrane removing forceps 300.

In one or more embodiments, particles having a first particle diameter may be fixed to a first portion of membrane removing forceps 300, e.g., particles having a first particle diameter of 5.0 micrometers may be fixed to a first portion of membrane removing forceps 300. Illustratively, a first abrasive surface 340 may comprise particles having the first particle diameter fixed to the first portion of membrane removing forceps 300. In one or more embodiments, particles having a second particle diameter may be fixed to a second portion of membrane removing forceps 300, e.g., particles having a second particle diameter of 10.0 micrometers may be fixed to a second portion of membrane removing forceps 300. Illustratively, a second abrasive surface 340 may comprise particles having the second particle diameter fixed to the second portion of membrane removing forceps 300. In one or more embodiments, particles having a third particle diameter may be fixed to a third portion of membrane removing forceps 300, e.g., particles having a third particle diameter of 15.0 micrometers may be fixed to a third portion of membrane removing forceps 300. Illustratively, a third abrasive surface 340 may comprise particles having the third particle diameter fixed to the third portion of membrane removing forceps 300. In one or more embodiments, particles having a fourth particle diameter may be fixed to a fourth portion of membrane removing forceps 300, e.g., particles having a is fourth particle diameter of 20.0 micrometers may be fixed to a fourth portion of membrane removing forceps 300. Illustratively, a fourth abrasive surface 340 may comprise particles having the fourth particle diameter fixed to the fourth portion of membrane removing forceps 300. In one or more embodiments, particles having a fifth particle diameter may be fixed to a fifth portion of membrane removing forceps 300, e.g., particles having a fifth particle diameter of 25.0 micrometers may be fixed to a fifth portion of membrane removing forceps 300. Illustratively, a fifth abrasive surface 340 may comprise particles having the fifth particle diameter fixed to the fifth portion of membrane removing forceps 300.

In one or more embodiments, a surgeon may select one or more particular abrasive surfaces 340 from a plurality of abrasive surfaces 340 of membrane removing forceps 300, e.g., to perform a surgical procedure. Illustratively, each particular abrasive surface 340 of a plurality of abrasive surfaces 340 may have one or more unique properties, e.g., each abrasive surface 340 may comprise particles having a unique particle diameter. In one or more embodiments, membrane removing forceps 300 may be configured to visually indicate to a surgeon a location of a particular abrasive surface 340, e.g., a location may be marked to indicate the presence of a particular abrasive surface 340 at the location. Illustratively, membrane removing forceps 300 may be configured to indicate to visually indicate to a surgeon one or more unique properties of an abrasive surface 340, e.g., a particular abrasive surface 340 may be marked to indicate one or more unique properties of the particular surface 340. In one or more embodiments, a surgeon may remove a membrane and minimize trauma to an underlying tissue by selecting an abrasive surface 340 of a membrane removing forceps 300, e.g., by manipulating an orientation of membrane removing forceps 300. Illustratively, a surgeon may select a first selected abrasive surface 340 of a plurality of abrasive surfaces 340 wherein the first selected abrasive surface 340 is configured to minimize an amount of trauma to the underlying tissue, e.g., a surgeon may select a first selected abrasive surface 340 of a plurality of abrasive surfaces 340 wherein the first selected abrasive surface 340 comprises particles having a first particle diameter. Illustratively, a surgeon may maneuver a portion of a first selected abrasive surface 340 across a portion of a membrane, e.g., to perform a first attempt to raise a portion of the membrane. If the first attempt to raise a portion of the membrane is unsuccessful, then the surgeon may select an abrasive surface 340 having particles with particle diameters larger than the particle diameters of the particles of the first selected abrasive surface 340, e.g., by manipulating an orientation of membrane removing forceps 300. In one or more embodiments, the surgeon may select a second selected abrasive surface 340 of a plurality of abrasive surfaces 340 wherein the second selected abrasive surface 340 is configured to minimize an amount of trauma to the underlying tissue, e.g., the surgeon may select a second selected abrasive surface 340 of a plurality of abrasive surfaces 340 wherein the second selected abrasive surface 340 comprises particles having a second particle diameter. Illustratively, the surgeon may maneuver a portion of a second selected abrasive surface 340 across a portion of a membrane, e.g., to perform a second attempt to raise a portion of the membrane. If the second attempt to raise a portion of the membrane is unsuccessful, then the surgeon may select an abrasive surface 340 having particles with particle diameters larger than the particle diameters of the particles of the second selected abrasive surface 340, e.g., by manipulating an orientation of membrane removing forceps 300. In one or more embodiments, the surgeon may select a third selected abrasive surface 340 of a plurality of abrasive surfaces 340 wherein the third selected abrasive surface 340 is configured to minimize an amount of trauma to the underlying tissue, e.g., the surgeon may select a third selected abrasive surface 340 of a plurality of abrasive surfaces 340 wherein the third selected abrasive surface 340 comprises particles having a third particle diameter. Illustratively, the surgeon may maneuver a portion of a third selected abrasive surface 340 across a portion of a membrane, e.g., to perform a third attempt to raise a portion of the membrane. If the third attempt to raise a portion of the membrane is unsuccessful, then the surgeon may select an abrasive surface 340 having particles with particle diameters larger than the particle diameters of the particles of the third selected abrasive surface 340, e.g., by manipulating an orientation of membrane removing forceps 300. In one or more embodiments, the surgeon may select a fourth selected abrasive surface 340 of a plurality of abrasive surfaces 340 wherein the fourth selected abrasive surface 340 is configured to minimize an amount of trauma to the underlying tissue, e.g., the surgeon may select a fourth selected abrasive surface 340 of a plurality of abrasive surfaces 340 wherein the fourth selected abrasive surface 340 comprises particles having a fourth particle diameter. Illustratively, the surgeon may maneuver a portion of a fourth selected abrasive surface 340 across a portion of a membrane, e.g., to perform a fourth attempt to raise a portion of the membrane. If the fourth attempt to raise a portion of the membrane is unsuccessful, then the surgeon may select an abrasive surface 340 having particles with particle diameters larger than the particle diameters of the particles of the fourth selected abrasive surface 340, e.g., by manipulating an orientation of membrane removing forceps 300. In one or more embodiments, the surgeon may select a fifth selected abrasive surface 340 of a plurality of abrasive surfaces 340 wherein the fifth selected abrasive surface 340 is configured to minimize an amount of trauma to the underlying tissue, e.g., the surgeon may select a fifth selected abrasive surface 340 of a plurality of abrasive surfaces 340 wherein the fifth selected abrasive surface 340 comprises particles having a fifth particle diameter. Illustratively, the surgeon may maneuver a portion of a fifth selected abrasive surface 340 across a portion of a membrane, e.g., to perform a fifth attempt to raise a portion of the membrane.

In one or more embodiments, abrasive surface 340 may be manufactured by modifying surgical blank 180, e.g., by an electric discharge machine. Illustratively, abrasive surface 340 may be manufactured by actuating a portion of surgical blank 180 relative to a wire of an electric discharge machine, e.g., to form a plurality of micropillars. In one or more embodiments, abrasive surface 340 may be manufactured by actuating a wire of an electric discharge machine relative to a portion of surgical blank 180, e.g., to form a plurality of micropillars. Illustratively, surgical blank 180 may be modified, e.g., by an electric discharge machine, wherein one or more portions of surgical blank 180 comprise a plurality of micropillars. In one or more embodiments, surgical blank 180 may be modified wherein one or more portions of surgical blank 180 comprise a plurality of micropillars and then surgical blank 180 may be modified to manufacture membrane removing forceps 300. Illustratively, one or more portions of membrane removing forceps 300 may comprise a plurality of micropillars. In one or more embodiments, surgical blank 180 may be modified to manufacture membrane removing forceps 300 and then membrane removing forceps 300 may be modified, e.g., by an electric discharge machine, wherein one or more portions of membrane removing forceps 300 comprise a plurality of micropillars.

Illustratively, abrasive surface 340 may be manufactured by modifying surgical blank 180, e.g., by laser ablation. In one or more embodiments, abrasive surface 340 may be manufactured by modifying surgical blank 180, e.g., by femtosecond laser ablation. Illustratively, abrasive surface 340 may be manufactured by applying laser energy to a portion of surgical blank 180 wherein the laser energy is applied in geometric patterns configured to fabricate micropillars on a surface of surgical blank 180, e.g., the laser energy may be applied in concentric circles, polygons, etc. In one or more embodiments, abrasive surface 340 may be manufactured by applying laser energy to a portion of surgical blank 180 wherein the laser energy is applied repeatedly in geometric patterns configured to fabricate micropillars on a surface of surgical blank 180, e.g., the laser energy may be repeatedly applied in concentric circles, polygons, etc. Illustratively, surgical blank 180 may be modified, e.g., by laser ablation, wherein one or more portions of surgical blank 180 comprise a plurality of micropillars. In one or more embodiments, surgical blank 180 may be modified wherein one or more portions of surgical blank 180 comprise a plurality of micropillars and then surgical blank 180 may be modified to manufacture membrane removing forceps 300. Illustratively, one or more portions of membrane removing forceps 300 may comprise a plurality of micropillars. In one or more embodiments, surgical blank 180 may be modified, e.g., by an electric discharge machine, to manufacture membrane removing forceps 300 and then membrane removing forceps 300 may be modified, e.g., by laser ablation, wherein one or more portions of membrane removing forceps 300 comprise a plurality of micropillars.

Illustratively, abrasive surface 340 may be manufactured by modifying surgical blank 180, e.g., by deep reactive-ion etching. In one or more embodiments, abrasive surface 340 may be manufactured by modifying surgical blank 180, e.g., by the Bosch process of time-multiplexed etching. Illustratively, abrasive surface 340 may be manufactured by exposing a portion of surgical blank 180 to repeated cycles of isotropic plasma etching followed by deposition of a chemically inert passivation layer to fabricate a plurality of micropillars on a surface of surgical blank 180. In one or more embodiments, abrasive surface 340 may be manufactured by fabricating a plurality of micropillars on a substrate and then fixing the substrate to a portion of surgical blank 180. Illustratively, surgical blank 180 may be modified, e.g., by deep reactive-ion etching, wherein one or more portions of surgical blank 180 comprise a plurality of micropillars. In one or more embodiments, surgical blank 180 may be modified wherein one or more portions of surgical blank 180 comprise a plurality of micropillars and then surgical blank 180 may be modified to manufacture membrane removing forceps 300. Illustratively, one or more portions of membrane removing forceps 300 may comprise a plurality of micropillars. In one or more embodiments, surgical blank 180 may be modified, e.g., by an electric discharge machine, to manufacture membrane removing forceps 300 and then membrane removing forceps 300 may be modified, e.g., by deep reactive-ion etching, wherein one or more portions of membrane removing forceps 300 comprise a plurality of micropillars.

Illustratively, abrasive surface 340 may comprise a plurality of micropillars, e.g., abrasive surface 340 may comprise one or more micropillar arrays. In one or more embodiments, abrasive surface 340 may comprise a plurality of micropillars having micropillar diameters in a range of 5.0 to 25.0 micrometers, e.g., abrasive surface 340 may comprise a plurality of micropillars having micropillar diameters of 15.0 micrometers. In one or more embodiments, abrasive surface 340 may comprise a plurality of micropillars having micropillar diameters less than 5.0 micrometers or greater than 25.0 micrometers. Illustratively, abrasive surface 340 may comprise a plurality of micropillars having micropillar heights in a range of 0.25 to 3.0 micrometers, e.g., abrasive surface 340 may comprise a plurality of micropillars having micropillar heights of 2.25 micrometers. In one or more embodiments, abrasive surface 340 may comprise a plurality of micropillars having micropillar heights less than 0.25 micrometers or greater than 3.0 micrometers. Illustratively, abrasive surface 340 may comprise a plurality of micropillars having micropillar heights in a range of 10.0 to 95.0 percent of the average thickness of internal limiting membrane 650, e.g., abrasive surface 340 may comprise a plurality of micropillars having micropillar heights of 80.0 percent of the average thickness of internal limiting membrane 650. In one or more embodiments, abrasive surface 340 may comprise a plurality of micropillars having micropillar orientations normal to a portion of a surface of membrane removing forceps 300. Illustratively, abrasive surface 340 may comprise a plurality of micropillars having micropillar orientations at an angle relative to a portion of a surface of membrane removing forceps 300. In one or more embodiments, abrasive surface 340 may comprise a plurality of micropillars having micropillar orientations at an angle in a range of 60.0 to 89.0 degrees relative to a portion of a surface of membrane removing forceps 300, e.g., abrasive surface 340 may comprise a plurality of micropillars having micropillar orientations at an angle of 85.0 degrees relative to a portion of a surface of membrane removing forceps 300. Illustratively, abrasive surface 340 may comprise a plurality of micropillars having micropillar orientations at an angle less than 60.0 degrees or greater than 89.0 degrees relative to a portion of a surface of membrane removing forceps 300.

In one or more embodiments, a first abrasive surface 340 of a plurality of abrasive surfaces 340 of membrane removing forceps 300 may comprise a plurality of micropillars having micropillar orientations at a first angle relative to a portion of a surface of membrane removing forceps 300, e.g., a first abrasive surface 340 of a plurality of abrasive surfaces 340 of membrane removing forceps 300 may comprise a plurality of micropillars having micropillar orientations at a 70.0 degree angle relative to a portion of a surface of membrane removing forceps 300. Illustratively, a second abrasive surface 340 of a plurality of abrasive surfaces 340 of membrane removing forceps 300 may comprise a plurality of micropillars having micropillar orientations at a second angle relative to a portion of a surface of membrane removing forceps 300, e.g., a second abrasive surface 340 of a plurality of abrasive surfaces 340 of membrane removing forceps 300 may comprise a plurality of micropillars having micropillar orientations at a 75.0 degree angle relative to a portion of a surface of membrane removing forceps 300. In one or more embodiments, a third abrasive surface 340 of a plurality of abrasive surfaces 340 of membrane removing forceps 300 may comprise a plurality of micropillars having micropillar orientations at a third angle relative to a portion of a surface of membrane removing forceps 300, e.g., a third abrasive surface 340 of a plurality of abrasive surfaces 340 of membrane removing forceps 300 may comprise a plurality of micropillars having micropillar orientations at an 80.0 degree angle relative to a portion of a surface of membrane removing forceps 300. Illustratively, a fourth abrasive surface 340 of a plurality of abrasive surfaces 340 of membrane removing forceps 300 may comprise a plurality of micropillars having micropillar orientations at a fourth angle relative to a portion of a surface of membrane removing forceps 300, e.g., a fourth abrasive surface 340 of a plurality of abrasive surfaces 340 of membrane removing forceps 300 may comprise a plurality of micropillars having micropillar orientations at an 85.0 degree angle relative to a portion of a surface of membrane removing forceps 300. In one or more embodiments, a fifth abrasive surface 340 of a plurality of abrasive surfaces 340 of membrane removing forceps 300 may comprise a plurality of micropillars having micropillar orientations at a fifth angle relative to a portion of a surface of membrane removing forceps 300, e.g., a fifth abrasive surface 340 of a plurality of abrasive surfaces 340 of membrane removing forceps 300 may comprise a plurality of micropillars having micropillar orientations at a 90.0 degree angle relative to a portion of a surface of membrane removing forceps 300.

In one or more embodiments, a surgeon may select one or more particular abrasive surfaces 340 from a plurality of abrasive surfaces 340 of membrane removing forceps 300, e.g., to perform a surgical procedure. Illustratively, each particular abrasive surface 340 of a plurality of abrasive surfaces 340 may have one or more unique properties, e.g., each abrasive surface 340 may comprise a plurality of micropillars having micropillar orientations at a particular angle relative to a portion of a surface of membrane removing forceps 300. In one or more embodiments, a surgeon may remove a membrane and minimize trauma to an underlying tissue by selecting an abrasive surface 340 of a membrane removing forceps 300, e.g., by manipulating an orientation of membrane removing forceps 300. Illustratively, a surgeon may select a first selected abrasive surface 340 of a plurality of abrasive surfaces 340 wherein the first selected abrasive surface 340 is configured to minimize an amount of trauma to the underlying tissue, e.g., a surgeon may select a first selected abrasive surface 340 of a plurality of abrasive surfaces 340 wherein the first selected abrasive surface 340 comprises a plurality of micropillars having micropillar orientations at a first angle relative to a portion of a surface of membrane removing forceps 300. In one or more embodiments, a surgeon may maneuver a portion of a first selected abrasive surface 340 across a portion of a membrane, e.g., to perform a first attempt to raise a portion of the membrane. If the first attempt to raise a portion of the membrane is unsuccessful, then the surgeon may select an abrasive surface 340 having a plurality of micropillars wherein the plurality of micropillars have micropillar orientations at an angle greater than the first angle relative to a portion of a surface of membrane removing forceps 300, e.g., by manipulating an orientation of membrane removing forceps 300. Illustratively, a surgeon may select a second selected abrasive surface 340 of a plurality of abrasive surfaces 340 wherein the second selected abrasive surface 340 is configured to minimize an amount of trauma to the underlying tissue, e.g., a surgeon may select a second selected abrasive surface 340 of a plurality of abrasive surfaces 340 wherein the second selected abrasive surface 340 comprises a plurality of micropillars having micropillar orientations at a second angle relative to a portion of a surface of membrane removing forceps 300. In one or more embodiments, a surgeon may maneuver a portion of a second selected abrasive surface 340 across a portion of a membrane, e.g., to perform a second attempt to raise a portion of the membrane. If the second attempt to raise a portion of the membrane is unsuccessful, then the surgeon may select an abrasive surface 340 having a plurality of micropillars wherein the plurality of micropillars have micropillar orientations at an angle greater than the second angle relative to a portion of a surface of membrane removing forceps 300, e.g., by manipulating an orientation of membrane removing forceps 300. Illustratively, a surgeon may select a third selected abrasive surface 340 of a plurality of abrasive surfaces 340 wherein the third selected abrasive surface 340 is configured to minimize an amount of trauma to the underlying tissue, e.g., a surgeon may select a third selected abrasive surface 340 of a plurality of abrasive surfaces 340 wherein the third selected abrasive surface 340 comprises a plurality of micropillars having micropillar orientations at a third angle relative to a portion of a surface of membrane removing forceps 300. In one or more embodiments, a surgeon may maneuver a portion of a third selected abrasive surface 340 across a portion of a membrane, e.g., to perform a third attempt to raise a portion of the membrane. If the third attempt to raise a portion of the membrane is unsuccessful, then the surgeon may select an abrasive surface 340 having a plurality of micropillars wherein the plurality of micropillars have micropillar orientations at an angle greater than the third angle relative to a portion of a surface of membrane removing forceps 300, e.g., by manipulating an orientation of membrane removing forceps 300. Illustratively, a surgeon may select a fourth selected abrasive surface 340 of a plurality of abrasive surfaces 340 wherein the fourth selected abrasive surface 340 is configured to minimize an amount of trauma to the underlying tissue, e.g., a surgeon may select a fourth selected abrasive surface 340 of a plurality of abrasive surfaces 340 wherein the fourth selected abrasive surface 340 comprises a plurality of micropillars having micropillar orientations at a fourth angle relative to a portion of a surface of membrane removing forceps 300. In one or more embodiments, a surgeon may maneuver a portion of a fourth selected abrasive surface 340 across a portion of a membrane, e.g., to perform a fourth attempt to raise a portion of the membrane. If the fourth attempt to raise a portion of the membrane is unsuccessful, then the surgeon may select an abrasive surface 340 having a plurality of micropillars wherein the plurality of micropillars have micropillar orientations at an angle greater than the fourth angle relative to a portion of a surface of membrane removing forceps 300, e.g., by manipulating an orientation of membrane removing forceps 300. Illustratively, a surgeon may select a fifth selected abrasive surface 340 of a plurality of abrasive surfaces 340 wherein the fifth selected abrasive surface 340 is configured to minimize an amount of trauma to the underlying tissue, e.g., a surgeon may select a fifth selected abrasive surface 340 of a plurality of abrasive surfaces 340 wherein the fifth selected abrasive surface 340 comprises a plurality of micropillars having micropillar orientations at a fifth angle relative to a portion of a surface of membrane removing forceps 300. In one or more embodiments, a surgeon may maneuver a portion of a fifth selected abrasive surface 340 across a portion of a membrane, e.g., to perform a fifth attempt to raise a portion of the membrane.

Illustratively, each forceps jaw 310 of a plurality of forceps jaws 310 may comprise a forceps jaw distal end 311 and a forceps jaw proximal end 312. In one or more embodiments, a first forceps jaw distal end 311 and a second forceps jaw distal end 311 may be separated by a maximum forceps jaw separation distance 315. Illustratively, a maximum forceps jaw separation distance 315 may be in a range of 0.005 to 0.08 inches, e.g., a maximum forceps jaw separation distance 315 may be 0.04 inches. In one or more embodiments, a maximum forceps jaw separation distance 315 may be less than 0.005 inches or greater than 0.08 inches. Illustratively, membrane removing forceps 300 may be configured to separate a first tissue from a surface of a second tissue without damaging the second tissue. For example, membrane removing forceps 300 may be configured to separate a first tissue having a convex surface geometry from a second tissue having a convex surface geometry without damaging the second tissue. In one or more embodiments, the first tissue may comprise an internal limiting membrane 650 and the second tissue may comprise a retinal tissue 670. Illustratively, a maximum forceps jaw separation distance 315 may be in a range of 200.0 to 600.0 times greater than an average thickness of the first tissue, e.g., a maximum forceps jaw separation distance 315 may be 291.0 times greater than an average thickness of the first tissue. In one or more embodiments, a maximum forceps jaw separation distance 315 may be less than 200.0 times or greater than 600.0 times greater than an average thickness of the first tissue. Illustratively, a maximum forceps jaw separation distance 315 may be in a range of 200.0 to 600.0 times greater than an average thickness of internal limiting membrane 650, e.g., a maximum forceps jaw separation distance 315 may be 291.0 times greater than an average thickness of internal limiting membrane 650. In one or more embodiments, a maximum forceps jaw separation distance 315 may be less than 200.0 times or greater than 600.0 times greater than an average thickness of internal limiting membrane 650.

Illustratively, first contour angle 320 may comprise any angle less than 90.0 degrees, e.g., first contour angle 320 may comprise any angle in a range of 60.0 to 80.0 degrees.

In one or more embodiments, first contour angle 320 may comprise an angle less than 60.0 degrees or greater than 80.0 degrees. Illustratively, first contour angle 320 may comprise a 76.3 degree angle. In one or more embodiments, second contour angle 330 may comprise any angle greater than 90.0 degrees, e.g., second contour angle 330 may comprise any angle in a range of 95.0 to 120.0 degrees. Illustratively, second contour angle 330 may comprise an angle less than 95.0 degrees or greater than 120.0 degrees. In one or more embodiments, second contour angle 330 may comprise a 103.7 degree angle.

In one or more embodiments, forceps jaws 310 may be configured to close at forceps jaws distal ends 311 as outer hypodermic tube 170 is gradually actuated over forceps jaws proximal ends 312. Illustratively, an extension of outer hypodermic tube 170 relative to surgical blank 180 may be configured to decrease a distance between a first forceps jaw distal end 311 and a second forceps jaw distal end 311. In one or more embodiments, an extension of outer hypodermic tube 170 over a first forceps jaw proximal end 312 and a second forceps jaw proximal end 312 may be configured to cause the first forceps jaw distal end 311 and the second forceps jaw distal end 311 to contact before any other portion of the first forceps jaw 310 contacts any other portion of the second forceps jaw 310.

FIGS. 4A, 4B, 4C, 4D, 4E, and 4F are schematic diagrams illustrating a gradual closing of a membrane removing forceps 300. FIG. 4A illustrates a top view and FIG. 4B illustrates a front view of an open membrane removing forceps 400. In one or more embodiments, membrane removing forceps 300 may comprise an open membrane removing forceps 400, e.g., when a first forceps jaw distal end 311 is separated from a second forceps jaw distal end 311 by maximum forceps jaw separation distance 315. Illustratively, membrane removing forceps 300 may comprise an open membrane removing forceps 400, e.g., when outer hypodermic tube 170 is fully retracted relative to forceps jaws proximal ends 312. Illustratively, membrane removing forceps 300 may comprise an open membrane removing forceps 400, e.g., when handle 110 is fully decompressed.

FIG. 4C illustrates a top view and FIG. 4D illustrates a front view of a partially closed membrane removing forceps 410. In one or more embodiments, a compression of handle 110 may be configured to gradually close a membrane removing forceps 300, e.g., from an open membrane removing forceps 400 to a partially closed membrane removing forceps 410. Illustratively, a compression of handle 110 may be configured to extend outer hypodermic tube 170 relative to surgical blank 180, e.g., a compression of handle 110 may be configured to extend outer hypodermic tube distal end 171 over forceps jaws proximal ends 312. In one or more embodiments, a compression of handle 110 may be configured to decrease a distance between a first forceps jaw distal end 311 and a second forceps jaw distal end 311, e.g., a first forceps jaw distal end 311 and a second forceps jaw distal end 311 may be separated by a distance less than maximum forceps jaw separation distance 315 when membrane removing forceps 300 comprises a partially closed membrane removing forceps 410.

FIG. 4E illustrates a top view and FIG. 4F illustrates a front view of a fully closed membrane removing forceps 420. Illustratively, a compression of handle 110 may be configured to gradually close a membrane removing forceps 300, e.g., from a partially closed membrane removing forceps 410 to a fully closed membrane removing forceps 420. In one or more embodiments, a compression of handle 110 may be configured to extend outer hypodermic tube 170 relative to surgical blank 180, e.g., a compression of handle 110 may be configured to extend outer hypodermic tube distal end 171 over forceps jaws proximal ends 312. Illustratively, an extension of outer hypodermic tube 170 over forceps jaws proximal ends 312 may be configured to close forceps jaws 310 wherein forceps jaws 310 initially contact at forceps jaws distal ends 311. In one or more embodiments, a compression of handle 110 may be configured to gradually close forceps jaws 310 wherein forceps jaws 310 initially contact at forceps jaws distal ends 311. Illustratively, after forceps jaws distal ends 311 initially contact, a compression of handle 110 may be configured to gradually close forceps jaws 310 wherein a contact area between forceps jaws 310 gradually increases. In one or more embodiments, forceps jaws 310 may be configured to close wherein an amount of a first forceps jaw 310 in contact with a second forceps jaw 310 increases gradually from forceps jaws distal ends 311, e.g., forceps jaws 310 may be configured to close wherein an amount of a first forceps jaw 310 in contact with a second forceps jaw 310 increases gradually towards forceps jaws proximal ends 312. Illustratively, a compression of handle 110 may be configured to close forceps jaws 310 starting at forceps jaws distal ends 311 and gradually progressing towards forceps jaws proximal ends 312. In one or more embodiments, a compression of handle 110 may be configured to close a first forceps jaw 310 and a second forceps jaw 310 wherein the first and second forceps jaws 310 initially contact each other at first and second forceps jaws distal ends 311. Illustratively, after the first and second forceps jaws 310 initially contact at first and second forceps jaws distal ends 311, a compression of handle 110 may be configured to cause medial portions of the first and second forceps jaws 310 to gradually contact each other starting at medial portions of the first and second forceps jaws 310 adjacent to first and second forceps jaws distal ends 311.

FIGS. 5A, 5B, 5C, 5D, 5E, and 5F are schematic diagrams illustrating a gradual opening of a membrane removing forceps 300. FIG. 5A illustrates a top view and FIG. 5B illustrates a front view of a closed membrane removing forceps 500. In one or more embodiments, membrane removing forceps 300 may comprise a closed membrane removing forceps 500, e.g., when a first forceps jaw distal end 311 is adjacent to a second forceps jaw distal end 311. Illustratively, membrane removing forceps 300 may comprise a closed membrane removing forceps 500, e.g., when outer hypodermic tube 170 is fully extended over forceps jaws proximal ends 312. Illustratively, membrane removing forceps 300 may comprise a closed membrane removing forceps 500, e.g., when handle 110 is fully compressed.

FIG. 5C illustrates a top view and FIG. 5D illustrates a front view of a partially open membrane removing forceps 510. In one or more embodiments, a decompression of handle 110 may be configured to gradually open a membrane removing forceps 300, e.g., from a closed membrane removing forceps 500 to a partially open membrane removing forceps 510. Illustratively, a decompression of handle 110 may be configured to retract outer hypodermic tube 170 relative to surgical blank 180, e.g., a decompression of handle 110 may be configured to retract outer hypodermic tube distal end 171 relative to forceps jaws proximal ends 312. In one or more embodiments, a decompression of handle 110 may be configured to gradually separate forceps jaws 310. Illustratively, a decompression of handle 110 may be configured to gradually separate forceps jaws 310 wherein a first forceps jaw distal end 311 contacts a second forceps jaw distal end 311 until all other portions of forceps jaws 310 are separated. In one or more embodiments, a decompression of handle 110 may be configured to separate forceps jaws 310 wherein forceps jaws distal ends 311 are the last portions of forceps jaws 310 to separate.

FIG. 5E illustrates a top view and FIG. 5F illustrates a front view of a fully open membrane removing forceps 520. Illustratively, a decompression of handle 110 may be configured to gradually open a membrane removing forceps 300, e.g., from a partially open membrane removing forceps 510 to a fully open membrane removing forceps 520. In one or more embodiments, a decompression of handle 110 may be configured to retract outer hypodermic tube 170 relative to surgical blank 180, e.g., a decompression of handle 110 may be configured to retract outer hypodermic tube distal end 171 relative to forceps jaws proximal ends 312. Illustratively, a decompression of handle 110 may be configured to gradually separate forceps jaws 310. In one or more embodiments, a first forceps jaw distal end 311 and a second forceps jaw distal end 311 may be separated by maximum forceps jaw separation distance 315, e.g., when membrane removing forceps 300 comprises a fully open membrane removing forceps 520.

Figure 6A:
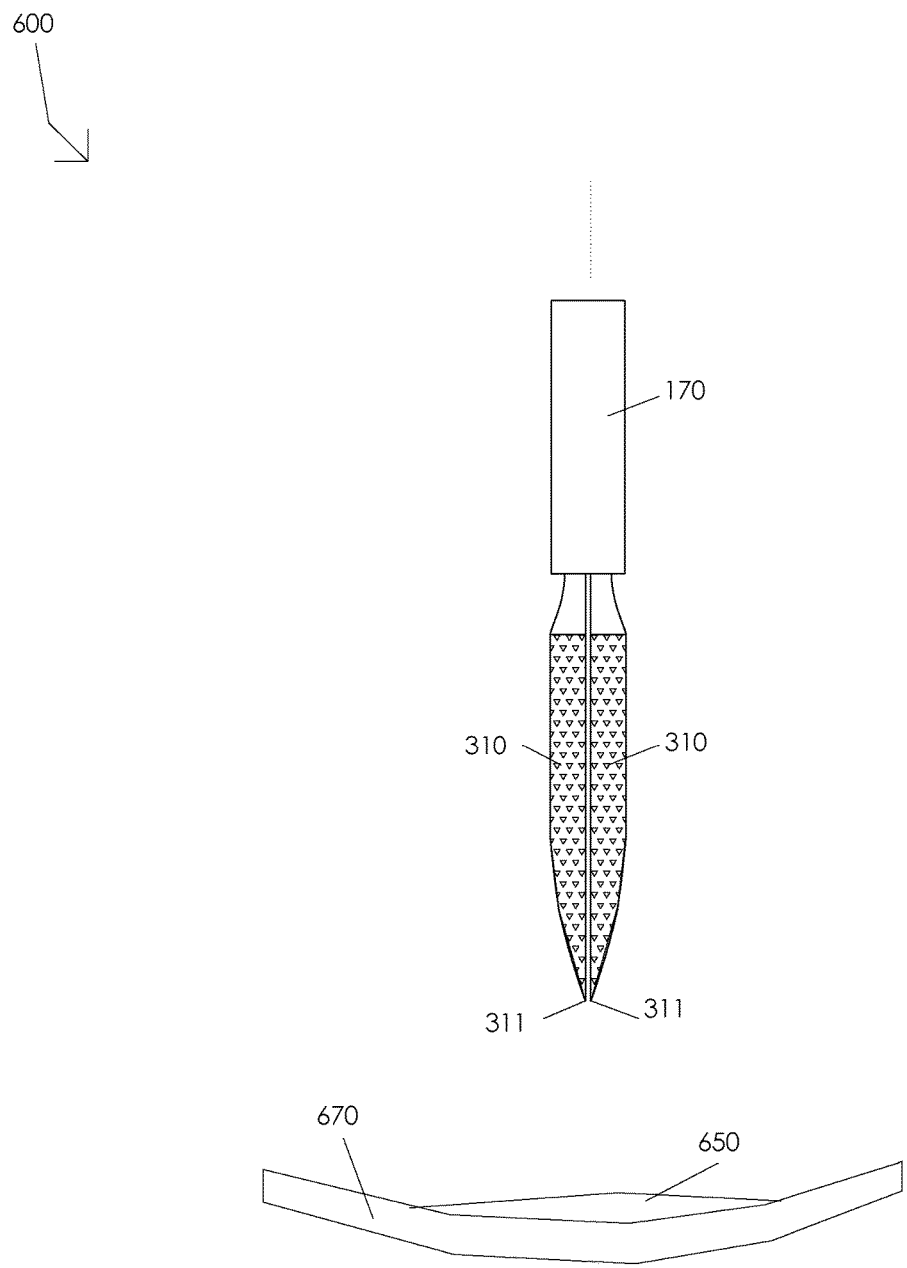
FIGS. 6A, 6B, 6C, 6D, and 6E are schematic diagrams illustrating a membrane removal.

FIGS. 6A, 6B, 6C, 6D, and 6E are schematic diagrams illustrating a membrane removal. FIG. 6A illustrates an attached membrane 600. Illustratively, an attached membrane 600 may comprise an internal limiting membrane 650 attached to a retinal tissue 670. In one or more embodiments, a surgeon may separate internal limiting membrane 650 from retinal tissue 670 by grasping internal limiting membrane 650 with forceps jaws 310, e.g., without damaging retinal tissue 670. Illustratively, a surgeon may manipulate handle 110 to approach retinal tissue 670 with membrane removing forceps 300, e.g., when membrane removing forceps 300 comprises an open membrane removing forceps 400. For example, a surgeon may gradually move forceps jaws distal ends 311 closer to retinal tissue 670 until forceps jaws distal ends 311 contact internal limiting membrane 650. In one or more embodiments, a compression of handle 110, e.g., by a surgeon, may be configured to extend outer hypodermic tube 170 over forceps jaws proximal ends 312. Illustratively, a surgeon may grasp internal limiting membrane 650 with forceps jaws distal ends 311 and no other portion of forceps jaws 310, e.g., to minimize trauma to an underlying retinal tissue 670. For example, after a surgeon grasps a first portion of internal limiting membrane 650 with forceps jaws distal ends 311, the surgeon may manipulate the first portion of internal limiting membrane 650 and compress handle 110 to grasp a second portion of limiting membrane 650 with forceps jaws 310. Illustratively, the surgeon may grasp the second portion of internal limiting membrane 650 with a portion of forceps jaws 310 located a distance from forceps jaws distal ends 311.

Figure 6B:
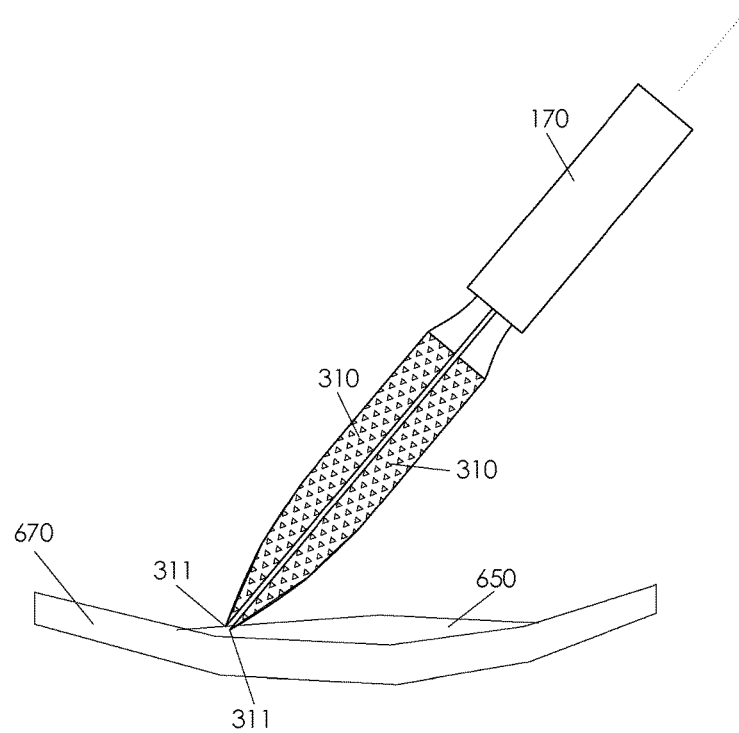

FIG. 6B illustrates a membrane grazing 610. In one or more embodiments, a membrane grazing 610 may be configured to raise a portion of a membrane, e.g., a membrane grazing 610 may be configured to raise a portion of internal limiting membrane 650. Illustratively, a membrane grazing 610 may comprise a contact between abrasive surface 340 and an internal limiting membrane 650. In one or more embodiments, abrasive surface 340 may be configured to grasp a portion of a membrane, e.g., internal limiting membrane 650. Illustratively, abrasive surface 340 may be configured to grasp and raise a portion of a membrane, e.g., internal limiting membrane 650. In one or more embodiments, abrasive surface 340 may be configured to grasp a portion of internal limiting membrane 650 and separate the portion of internal limiting membrane 650 from a portion of retinal tissue 670. Illustratively, a surgeon may maneuver a portion of abrasive surface 340 across a portion of a membrane, e.g., a surgeon may maneuver a portion of abrasive surface 340 across a portion of internal limiting membrane 650. In one or more embodiments, as a surgeon maneuvers a portion of abrasive surface 340 across a portion of internal limiting membrane 650, the surgeon may graze the portion of internal limiting membrane 650, e.g., by contacting the portion of internal limiting membrane 650 with abrasive surface 340. Illustratively, a contact between abrasive surface 340 and a portion of internal limiting membrane 650 may be configured to grasp the portion of internal limiting membrane 650. In one or more embodiments, a contact between abrasive surface 340 and a portion of internal limiting membrane 650 may be configured to grasp and raise the portion of internal limiting membrane 650. Illustratively, a surgeon may graze a portion of internal limiting membrane 650, e.g., by contacting abrasive surface 340 and a portion of internal limiting membrane 650 to grasp the portion of internal limiting membrane 650 and then actuating abrasive surface 340 relative to internal limiting membrane 650 to raise the portion of internal limiting membrane 650.

Figure 6C:
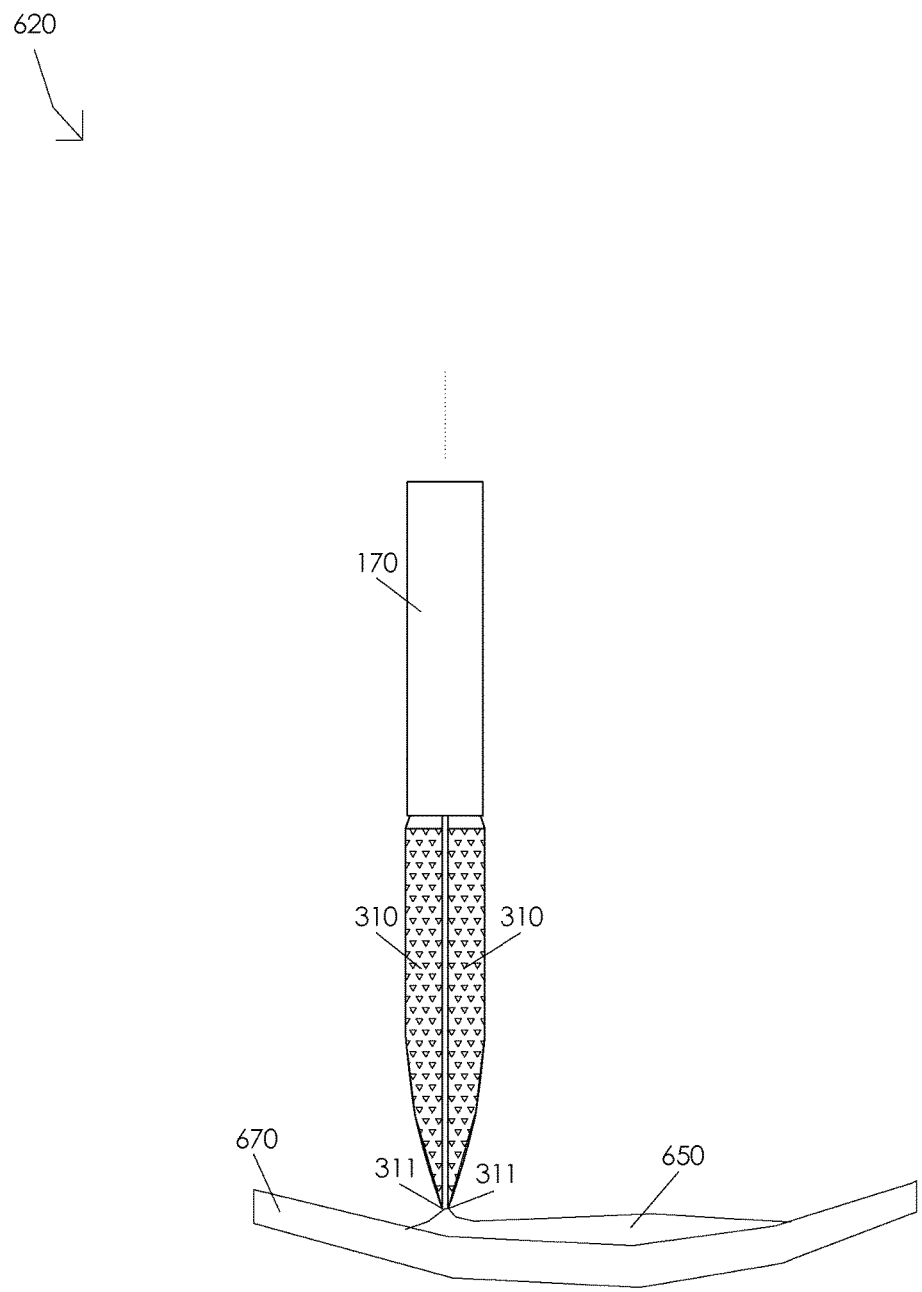

FIG. 6C illustrates a grasping of a raised portion of a membrane 620. Illustratively, a surgeon may grasp a portion of a membrane, e.g., a raised portion of internal limiting membrane 650, with membrane removing forceps 300 by compressing handle 110. In one or more embodiments, a surgeon may grasp a portion of a membrane, e.g., a raised portion of internal limiting membrane 650, by disposing the portion of the membrane in between forceps jaws 310 and compressing handle 110. Illustratively, a surgeon may raise a portion of internal limiting membrane 650, e.g., by performing a membrane grazing 610. In one or more embodiments, a surgeon may grasp the raised portion of internal limiting membrane 650, e.g., by maneuvering forceps jaws 310 wherein the raised portion of internal limiting membrane 650 is disposed between forceps jaws distal ends 311. Illustratively, a surgeon may grasp a raised portion of internal limiting membrane 650 disposed between forceps jaws distal ends 311, e.g., by compressing handle 110.

Figure 6D:
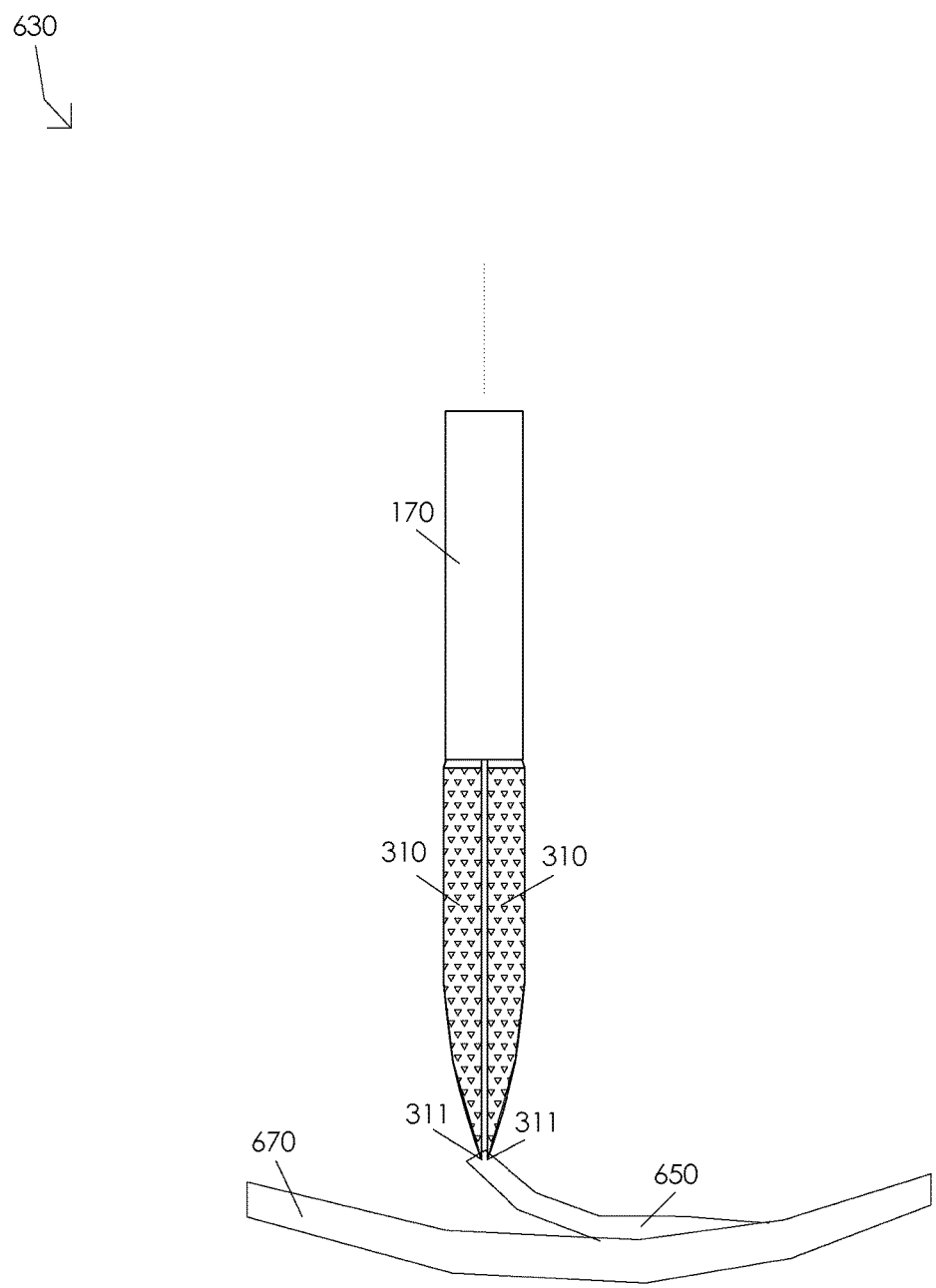

FIG. 6D illustrates a partially peeled membrane 630. Illustratively, a partially peeled membrane 630 may comprise an internal limiting membrane 650 partially separated from a retinal tissue 670. In one or more embodiments, a surgeon may raise a portion of a membrane, e.g., an internal limiting membrane 650, by performing a membrane grazing 610. Illustratively, a surgeon may grasp a raised portion of a membrane, e.g., an internal limiting membrane 650, by performing a grasping of a raised portion of a membrane 620. In one or more embodiments, a surgeon may peel a membrane apart from an underlying tissue by grasping the membrane with membrane removing forceps 300 and pulling the membrane apart from the underlying tissue. Illustratively, a surgeon may peel an internal limiting membrane 650 apart from an underlying retinal tissue 670 by grasping internal limiting membrane 650 with membrane removing forceps 300 and pulling internal limiting membrane 650 apart from retinal tissue 670. In one or more embodiments, a surgeon may peel a membrane apart from an underlying tissue by grasping the membrane with membrane removing forceps 300 and pulling the membrane apart from the underlying tissue until the membrane comprises a partially peeled membrane 630. Illustratively, a surgeon may peel an internal limiting membrane 650 apart from an underlying retinal tissue 670 by grasping internal limiting membrane 650 with membrane removing forceps 300 and pulling internal limiting membrane 650 apart from retinal tissue 670 until internal limiting membrane 650 comprises a partially peeled membrane 630.

Figure 6E:
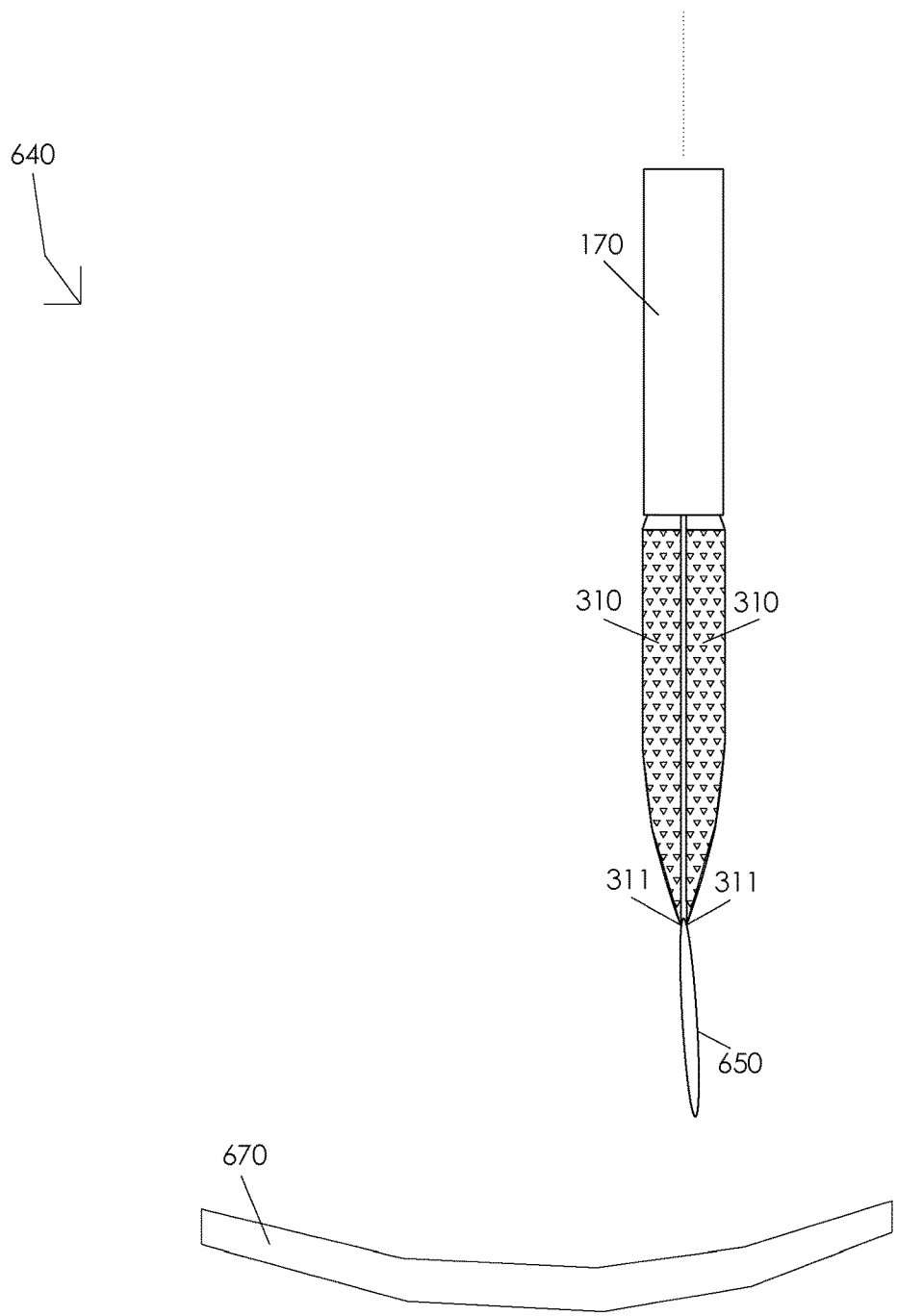

FIG. 6E illustrates a fully peeled membrane 640. Illustratively, a fully peeled membrane 640 may comprise an internal limiting membrane 650 completely separated from a retinal tissue 670. In one or more embodiments, a surgeon may peel a membrane apart from an underlying tissue by grasping the membrane with membrane removing forceps 300 and pulling the membrane apart from the underlying tissue until the membrane comprises a fully peeled membrane 640. Illustratively, a surgeon may continue to peel a partially peeled membrane 630 apart from an underlying tissue until the membrane comprises a fully peeled membrane 640. In one or more embodiments, a surgeon may peel an internal limiting membrane 650 apart from an underlying retinal tissue 670 by grasping internal limiting membrane 650 with membrane removing forceps 300 and pulling internal limiting membrane 650 apart from retinal tissue 670 until internal limiting membrane 650 comprises a fully peeled membrane 640. Illustratively, a surgeon may continue to peel a partially peeled membrane 630 apart from retinal tissue 670 until internal limiting membrane 650 comprises a fully peeled membrane 640.

FIGS. 7A and 7B are schematic diagrams illustrating a blunt-tip membrane removing forceps 700. FIG. 7A illustrates a top view and FIG. 7B illustrates a front view of a blunt-tip membrane removing forceps 700. Illustratively, blunt-tip membrane removing forceps 700 may be manufactured with dimensions configured for performing microsurgical procedures, e.g., ophthalmic surgical procedures. In one or more embodiments, blunt-tip membrane removing forceps 700 may be manufactured from surgical blank 180. Illustratively, blunt-tip membrane removing forceps 700 may be manufactured by modifying surgical blank 180, e.g., with an electric discharge machine. In one or more embodiments, blunt-tip membrane removing forceps 700 may be manufactured by modifying surgical blank 180, e.g., with a laser, a file, or any suitable modification means. Illustratively, blunt-tip membrane removing forceps 700 may comprise a plurality of forceps jaws 710, a third contour angle 720, a fourth contour angle 730, and one or more abrasive surfaces 740.

In one or more embodiments, abrasive surface 740 may be configured to grasp a portion of a membrane, e.g., abrasive surface 740 may be configured to grasp a portion of an internal limiting membrane 650. Illustratively, a surgeon may maneuver a portion of abrasive surface 740 across a portion of a membrane, e.g., to raise a portion of the membrane. In one or more embodiments, abrasive surface 740 may be configured to grasp a portion of a first tissue disposed over a second tissue without damaging the second tissue. Illustratively, abrasive surface 740 may be configured to grasp a first tissue having a convex surface geometry disposed over a second tissue having a convex surface geometry without damaging the second tissue.

In one or more embodiments, abrasive surface 740 may be manufactured by fixing particles, e.g., inert particles, to a portion of blunt-tip membrane removing forceps 700. Illustratively, particles may be fixed to a portion of blunt-tip membrane removing forceps 700, e.g., by an adhesive or any suitable fixation means. In one or more embodiments, particles may be fixed to a portion of blunt-tip membrane removing forceps 700 by a biocompatible high temperature epoxy. Illustratively, particles may be fixed to a portion of blunt-tip membrane removing forceps 700 by a biocompatible spectrally transparent epoxy. In one or more embodiments, a portion of blunt-tip membrane removing forceps 700 may be coated by a material configured to facilitate adhesion of particles. Illustratively, a portion of blunt-tip membrane removing forceps 700 may be coated by a material, e.g., silicon, and then particles may be fixed to the material, e.g., by an adhesive or any suitable fixation means.

In one or more embodiments, abrasive surface 740 may be manufactured by fixing particles to a portion of blunt-tip membrane removing forceps 700, e.g., particles may comprise diamond particles, sapphire particles, ruby particles, emerald particles, etc. Illustratively, abrasive surface 740 may be manufactured by fixing biocompatible particles to a portion of blunt-tip membrane removing forceps 700. In one or more embodiments, abrasive surface 740 may be manufactured by fixing particles having particle diameters in a range of 5.0 to 25.0 micrometers to a portion of blunt-tip membrane removing forceps 700, e.g., abrasive surface 740 may be manufactured by fixing particles having particle diameters of 15.0 micrometers to a portion of blunt-tip membrane removing forceps 700. Illustratively, abrasive surface 740 may be manufactured by fixing particles having particle diameters less than 5.0 micrometers or greater than 25.0 micrometers to a portion of blunt-tip membrane removing forceps 700.

In one or more embodiments, particles having a first particle diameter may be fixed to a first portion of blunt-tip membrane removing forceps 700, e.g., particles having a first particle diameter of 5.0 micrometers may be fixed to a first portion of blunt-tip membrane removing forceps 700. Illustratively, a first abrasive surface 740 may comprise particles having the first particle diameter fixed to the first portion of blunt-tip membrane removing forceps 700. In one or more embodiments, particles having a second particle diameter may be fixed to a second portion of blunt-tip membrane removing forceps 700, e.g., particles having a second particle diameter of 10.0 micrometers may be fixed to a second portion of blunt-tip membrane removing forceps 700. Illustratively, a second abrasive surface 740 may comprise particles having the second particle diameter fixed to the second portion of blunt-tip membrane removing forceps 700. In one or more embodiments, particles having a third particle diameter may be fixed to a third portion of blunt-tip membrane removing forceps 700, e.g., particles having a third particle diameter of 15.0 micrometers may be fixed to a third portion of blunt-tip membrane removing forceps 700. Illustratively, a third abrasive surface 740 may comprise particles having the third particle diameter fixed to the third portion of blunt-tip membrane removing forceps 700. In one or more embodiments, particles having a fourth particle diameter may be fixed to a fourth portion of blunt-tip membrane removing forceps 700, e.g., particles having a fourth particle diameter of 20.0 micrometers may be fixed to a fourth portion of blunt-tip membrane removing forceps 700. Illustratively, a fourth abrasive surface 740 may comprise particles having the fourth particle diameter fixed to the fourth portion of blunt-tip membrane removing forceps 700. In one or more embodiments, particles having a fifth particle diameter may be fixed to a fifth portion of blunt-tip membrane removing forceps 700, e.g., particles having a fifth particle diameter of 25.0 micrometers may be fixed to a fifth portion of blunt-tip membrane removing forceps 700. Illustratively, a fifth abrasive surface 740 may comprise particles having the fifth particle diameter fixed to the fifth portion of blunt-tip membrane removing forceps 700.

In one or more embodiments, a surgeon may select one or more particular abrasive surfaces 740 from a plurality of abrasive surfaces 740 of blunt-tip membrane removing forceps 700, e.g., to perform a surgical procedure. Illustratively, each particular abrasive surface 740 of a plurality of abrasive surfaces 740 may have one or more unique properties, e.g., each abrasive surface 740 may comprise particles having a unique particle diameter. In one or more embodiments, a surgeon may remove a membrane and minimize trauma to an underlying tissue by selecting an abrasive surface 740 of a blunt-tip membrane removing forceps 700, e.g., by manipulating an orientation of blunt-tip membrane removing forceps 700. Illustratively, a surgeon may select a first selected abrasive surface 740 of a plurality of abrasive surfaces 740 wherein the first selected abrasive surface 740 is configured to minimize an amount of trauma to the underlying tissue, e.g., a surgeon may select a first selected abrasive surface 740 of a plurality of abrasive surfaces 740 wherein the first selected abrasive surface 740 comprises particles having a first particle diameter. Illustratively, a surgeon may maneuver a portion of a first selected abrasive surface 740 across a portion of a membrane, e.g., to perform a first attempt to raise a portion of the membrane. If the first attempt to raise a portion of the membrane is unsuccessful, then the surgeon may select an abrasive surface 740 having particles with particle diameters larger than the particle diameters of the particles of the first selected abrasive surface 740, e.g., by manipulating an orientation of blunt-tip membrane removing forceps 700. In one or more embodiments, the surgeon may select a second selected abrasive surface 740 of a plurality of abrasive surfaces 740 wherein the second selected abrasive surface 740 is configured to minimize an amount of trauma to the underlying tissue, e.g., the surgeon may select a second selected abrasive surface 740 of a plurality of abrasive surfaces 740 wherein the second selected abrasive surface 740 comprises particles having a second particle diameter. Illustratively, the surgeon may maneuver a portion of a second selected abrasive surface 740 across a portion of a membrane, e.g., to perform a second attempt to raise a portion of the membrane. If the second attempt to raise a portion of the membrane is unsuccessful, then the surgeon may select an abrasive surface 740 having particles with particle diameters larger than the particle diameters of the particles of the second selected abrasive surface 740, e.g., by manipulating an orientation of blunt-tip membrane removing forceps 700. In one or more embodiments, the surgeon may select a third selected abrasive surface 740 of a plurality of abrasive surfaces 740 wherein the third selected abrasive surface 740 is configured to minimize an amount of trauma to the underlying tissue, e.g., the surgeon may select a third selected abrasive surface 740 of a plurality of abrasive surfaces 740 wherein the third selected abrasive surface 740 comprises particles having a third particle diameter. Illustratively, the surgeon may maneuver a portion of a third selected abrasive surface 740 across a portion of a membrane, e.g., to perform a third attempt to raise a portion of the membrane. If the third attempt to raise a portion of the membrane is unsuccessful, then the surgeon may select an abrasive surface 740 having particles with particle diameters larger than the particle diameters of the particles of the third selected abrasive surface 740, e.g., by manipulating an orientation of blunt-tip membrane removing forceps 700. In one or more embodiments, the surgeon may select a fourth selected abrasive surface 740 of a plurality of abrasive surfaces 740 wherein the fourth selected abrasive surface 740 is configured to minimize an amount of trauma to the underlying tissue, e.g., the surgeon may select a fourth selected abrasive surface 740 of a plurality of abrasive surfaces 740 wherein the fourth selected abrasive surface 740 comprises particles having a fourth particle diameter. Illustratively, the surgeon may maneuver a portion of a fourth selected abrasive surface 740 across a portion of a membrane, e.g., to perform a fourth attempt to raise a portion of the membrane. If the fourth attempt to raise a portion of the membrane is unsuccessful, then the surgeon may select an abrasive surface 740 having particles with particle diameters larger than the particle diameters of the particles of the fourth selected abrasive surface 740, e.g., by manipulating an orientation of blunt-tip membrane removing forceps 700. In one or more embodiments, the surgeon may select a fifth selected abrasive surface 740 of a plurality of abrasive surfaces 740 wherein the fifth selected abrasive surface 740 is configured to minimize an amount of trauma to the underlying tissue, e.g., the surgeon may select a fifth selected abrasive surface 740 of a plurality of abrasive surfaces 740 wherein the fifth selected abrasive surface 740 comprises particles having a fifth particle diameter. Illustratively, the surgeon may maneuver a portion of a fifth selected abrasive surface 740 across a portion of a membrane, e.g., to perform a fifth attempt to raise a portion of the membrane.

In one or more embodiments, abrasive surface 740 may be manufactured by modifying surgical blank 180, e.g., by an electric discharge machine. Illustratively, abrasive surface 740 may be manufactured by actuating a portion of surgical blank 180 relative to a wire of an electric discharge machine, e.g., to form a plurality of micropillars. In one or more embodiments, abrasive surface 740 may be manufactured by actuating a wire of an electric discharge machine relative to a portion of surgical blank 180, e.g., to form a plurality of micropillars. Illustratively, surgical blank 180 may be modified, e.g., by an electric discharge machine, wherein one or more portions of surgical blank 180 comprise a plurality of micropillars. In one or more embodiments, surgical blank 180 may be modified wherein one or more portions of surgical blank 180 comprise a plurality of micropillars and then surgical blank 180 may be modified to manufacture blunt-tip membrane removing forceps 700. Illustratively, one or more portions of blunt-tip membrane removing forceps 700 may comprise a plurality of micropillars. In one or more embodiments, surgical blank 180 may be modified to manufacture blunt-tip membrane removing forceps 700 and then blunt-tip membrane removing forceps 700 may be modified, e.g., by an electric discharge machine, wherein one or more portions of blunt-tip membrane removing forceps 700 comprise a plurality of micropillars.

Illustratively, abrasive surface 740 may be manufactured by modifying surgical blank 180, e.g., by laser ablation. In one or more embodiments, abrasive surface 740 may be manufactured by modifying surgical blank 180, e.g., by femtosecond laser ablation. Illustratively, abrasive surface 740 may be manufactured by applying laser energy to a portion of surgical blank 180 wherein the laser energy is applied in geometric patterns configured to fabricate micropillars on a surface of surgical blank 180, e.g., the laser energy may be applied in concentric circles, polygons, etc. In one or more embodiments, abrasive surface 740 may be manufactured by applying laser energy to a portion of surgical blank 180 wherein the laser energy is applied repeatedly in geometric patterns configured to fabricate micropillars on a surface of surgical blank 180, e.g., the laser energy may be repeatedly applied in concentric circles, polygons, etc. Illustratively, surgical blank 180 may be modified, e.g., by laser ablation, wherein one or more portions of surgical blank 180 comprise a plurality of micropillars. In one or more embodiments, surgical blank 180 may be modified wherein one or more portions of surgical blank 180 comprise a plurality of micropillars and then surgical blank 180 may be modified to manufacture blunt-tip membrane removing forceps 700. Illustratively, one or more portions of blunt-tip membrane removing forceps 700 may comprise a plurality of micropillars. In one or more embodiments, surgical blank 180 may be modified, e.g., by an electric discharge machine, to manufacture blunt-tip membrane removing forceps 700 and then blunt-tip membrane removing forceps 700 may be modified, e.g., by laser ablation, wherein one or more portions of blunt-tip membrane removing forceps 700 comprise a plurality of micropillars.

Illustratively, abrasive surface 740 may be manufactured by modifying surgical blank 180, e.g., by deep reactive-ion etching. In one or more embodiments, abrasive surface 740 may be manufactured by modifying surgical blank 180, e.g., by the Bosch process of time-multiplexed etching. Illustratively, abrasive surface 740 may be manufactured by exposing a portion of surgical blank 180 to repeated cycles of isotropic plasma etching followed by deposition of a chemically inert passivation layer to fabricate a plurality of micropillars on a surface of surgical blank 180. In one or more embodiments, abrasive surface 740 may be manufactured by fabricating a plurality of micropillars on a substrate and then fixing the substrate to a portion of surgical blank 180. Illustratively, surgical blank 180 may be modified, e.g., by deep reactive-ion etching, wherein one or more portions of surgical blank 180 comprise a plurality of micropillars. In one or more embodiments, surgical blank 180 may be modified wherein one or more portions of surgical blank 180 comprise a plurality of micropillars and then surgical blank 180 may be modified to manufacture blunt-tip membrane removing forceps 700. Illustratively, one or more portions of blunt-tip membrane removing forceps 700 may comprise a plurality of micropillars. In one or more embodiments, surgical blank 180 may be modified, e.g., by an electric discharge machine, to manufacture blunt-tip membrane removing forceps 700 and then blunt-tip membrane removing forceps 700 may be modified, e.g., by deep reactive-ion etching, wherein one or more portions of blunt-tip membrane removing forceps 700 comprise a plurality of micropillars.

Illustratively, abrasive surface 740 may comprise a plurality of micropillars, e.g., abrasive surface 740 may comprise one or more micropillar arrays. In one or more embodiments, abrasive surface 740 may comprise a plurality of micropillars having micropillar diameters in a range of 5.0 to 25.0 micrometers, e.g., abrasive surface 740 may comprise a plurality of micropillars having micropillar diameters of 15.0 micrometers. In one or more embodiments, abrasive surface 740 may comprise a plurality of micropillars having micropillar diameters less than 5.0 micrometers or greater than 25.0 micrometers. Illustratively, abrasive surface 740 may comprise a plurality of micropillars having micropillar heights in a range of 0.25 to 3.0 micrometers, e.g., abrasive surface 740 may comprise a plurality of micropillars having micropillar heights of 2.25 micrometers. In one or more embodiments, abrasive surface 740 may comprise a plurality of micropillars having micropillar heights less than 0.25 micrometers or greater than 3.0 micrometers. Illustratively, abrasive surface 740 may comprise a plurality of micropillars having micropillar heights in a range of 10.0 to 95.0 percent of the average thickness of internal limiting membrane 650, e.g., abrasive surface 740 may comprise a plurality of micropillars having micropillar heights of 80.0 percent of the average thickness of internal limiting membrane 650. In one or more embodiments, abrasive surface 740 may comprise a plurality of micropillars having micropillar orientations normal to a portion of a surface of blunt-tip membrane removing forceps 700. Illustratively, abrasive surface 740 may comprise a plurality of micropillars having micropillar orientations at an angle relative to a portion of a surface of blunt-tip membrane removing forceps 700. In one or more embodiments, abrasive surface 740 may comprise a plurality of micropillars having micropillar orientations at an angle in a range of 60.0 to 89.0 degrees relative to a portion of a surface of blunt-tip membrane removing forceps 700, e.g., abrasive surface 740 may comprise a plurality of micropillars having micropillar orientations at an angle of 85.0 degrees relative to a portion of a surface of blunt-tip membrane removing forceps 700. Illustratively, abrasive surface 740 may comprise a plurality of micropillars having micropillar orientations at an angle less than 60.0 degrees or greater than 89.0 degrees relative to a portion of a surface of blunt-tip membrane removing forceps 700.

In one or more embodiments, a first abrasive surface 740 of a plurality of abrasive surfaces 740 of membrane removing forceps 700 may comprise a plurality of micropillars having micropillar orientations at a first angle relative to a portion of a surface of blunt-tip membrane removing forceps 700, e.g., a first abrasive surface 740 of a plurality of abrasive surfaces 740 of blunt-tip membrane removing forceps 700 may comprise a plurality of micropillars having micropillar orientations at a 70.0 degree angle relative to a portion of a surface of blunt-tip membrane removing forceps 700. Illustratively, a second abrasive surface 740 of a plurality of abrasive surfaces 740 of blunt-tip membrane removing forceps 700 may comprise a plurality of micropillars having micropillar orientations at a second angle relative to a portion of a surface of blunt-tip membrane removing forceps 700, e.g., a second abrasive surface 740 of a plurality of abrasive surfaces 740 of blunt-tip membrane removing forceps 700 may comprise a plurality of micropillars having micropillar orientations at a 75.0 degree angle relative to a portion of a surface of blunt-tip membrane removing forceps 700. In one or more embodiments, a third abrasive surface 740 of a plurality of abrasive surfaces 740 of blunt-tip membrane removing forceps 700 may comprise a plurality of micropillars having micropillar orientations at a third angle relative to a portion of a surface of blunt-tip membrane removing forceps 700, e.g., a third abrasive surface 740 of a plurality of abrasive surfaces 740 of blunt-tip membrane removing forceps 700 may comprise a plurality of micropillars having micropillar orientations at an 80.0 degree angle relative to a portion of a surface of blunt-tip membrane removing forceps 700. Illustratively, a fourth abrasive surface 740 of a plurality of abrasive surfaces 740 of blunt-tip membrane removing forceps 700 may comprise a plurality of micropillars having micropillar orientations at a fourth angle relative to a portion of a surface of blunt-tip membrane removing forceps 700, e.g., a fourth abrasive surface 740 of a plurality of abrasive surfaces 740 of blunt-tip membrane removing forceps 700 may comprise a plurality of micropillars having micropillar orientations at an 85.0 degree angle relative to a portion of a surface of blunt-tip membrane removing forceps 700. In one or more embodiments, a fifth abrasive surface 740 of a plurality of abrasive surfaces 740 of blunt-tip membrane removing forceps 700 may comprise a plurality of micropillars having micropillar orientations at a fifth angle relative to a portion of a surface of blunt-tip membrane removing forceps 700, e.g., a fifth abrasive surface 740 of a plurality of abrasive surfaces 740 of blunt-tip membrane removing forceps 700 may comprise a plurality of micropillars having micropillar orientations at a 90.0 degree angle relative to a portion of a surface of blunt-tip membrane removing forceps 700.

In one or more embodiments, a surgeon may select one or more particular abrasive surfaces 740 from a plurality of abrasive surfaces 740 of blunt-tip membrane removing forceps 700, e.g., to perform a surgical procedure. Illustratively, each particular abrasive surface 740 of a plurality of abrasive surfaces 740 may have one or more unique properties, e.g., each abrasive surface 740 may comprise a plurality of micropillars having micropillar orientations at a particular angle relative to a portion of a surface of blunt-tip membrane removing forceps 700. In one or more embodiments, membrane removing forceps 700 may be configured to visually indicate to a surgeon a location of a particular abrasive surface 740, e.g., a location may be marked to indicate the presence of a particular abrasive surface 740 at the location. Illustratively, membrane removing forceps 700 may be configured to indicate to visually indicate to a surgeon one or more unique properties of an abrasive surface 740, e.g., a particular abrasive surface 740 may be marked to indicate one or more unique properties of the particular surface 740. In one or more embodiments, a surgeon may remove a membrane and minimize trauma to an underlying tissue by selecting an abrasive surface 740 of a blunt-tip membrane removing forceps 700, e.g., by manipulating an orientation of blunt-tip membrane removing forceps 700. Illustratively, a surgeon may select a first selected abrasive surface 740 of a plurality of abrasive surfaces 740 wherein the first selected abrasive surface 740 is configured to minimize an amount of trauma to the underlying tissue, e.g., a surgeon may select a first selected abrasive surface 740 of a plurality of abrasive surfaces 740 wherein the first selected abrasive surface 740 comprises a plurality of micropillars having micropillar orientations at a first angle relative to a portion of a surface of blunt-tip membrane removing forceps 700. In one or more embodiments, a surgeon may maneuver a portion of a first selected abrasive surface 740 across a portion of a membrane, e.g., to perform a first attempt to raise a portion of the membrane. If the first attempt to raise a portion of the membrane is unsuccessful, then the surgeon may select an abrasive surface 740 having a plurality of micropillars wherein the plurality of micropillars have micropillar orientations at an angle greater than the first angle relative to a portion of a surface of blunt-tip membrane removing forceps 700, e.g., by manipulating an orientation of blunt-tip membrane removing forceps 700. Illustratively, a surgeon may select a second selected abrasive surface 740 of a plurality of abrasive surfaces 740 wherein the second selected abrasive surface 740 is configured to minimize an amount of trauma to the underlying tissue, e.g., a surgeon may select a second selected abrasive surface 740 of a plurality of abrasive surfaces 740 wherein the second selected abrasive surface 740 comprises a plurality of micropillars having micropillar orientations at a second angle relative to a portion of a surface of blunt-tip membrane removing forceps 700. In one or more embodiments, a surgeon may maneuver a portion of a second selected abrasive surface 740 across a portion of a membrane, e.g., to perform a second attempt to raise a portion of the membrane. If the second attempt to raise a portion of the membrane is unsuccessful, then the surgeon may select an abrasive surface 740 having a plurality of micropillars wherein the plurality of micropillars have micropillar orientations at an angle greater than the second angle relative to a portion of a surface of blunt-tip membrane removing forceps 700, e.g., by manipulating an orientation of blunt-tip membrane removing forceps 700. Illustratively, a surgeon may select a third selected abrasive surface 740 of a plurality of abrasive surfaces 740 wherein the third selected abrasive surface 740 is configured to minimize an amount of trauma to the underlying tissue, e.g., a surgeon may select a third selected abrasive surface 740 of a plurality of abrasive surfaces 740 wherein the third selected abrasive surface 740 comprises a plurality of micropillars having micropillar orientations at a third angle relative to a portion of a surface of blunt-tip membrane removing forceps 700. In one or more embodiments, a surgeon may maneuver a portion of a third selected abrasive surface 740 across a portion of a membrane, e.g., to perform a third attempt to raise a portion of the membrane. If the third attempt to raise a portion of the membrane is unsuccessful, then the surgeon may select an abrasive surface 740 having a plurality of micropillars wherein the plurality of micropillars have micropillar orientations at an angle greater than the third angle relative to a portion of a surface of blunt-tip membrane removing forceps 700, e.g., by manipulating an orientation of blunt-tip membrane removing forceps 700. Illustratively, a surgeon may select a fourth selected abrasive surface 740 of a plurality of abrasive surfaces 740 wherein the fourth selected abrasive surface 740 is configured to minimize an amount of trauma to the underlying tissue, e.g., a surgeon may select a fourth selected abrasive surface 740 of a plurality of abrasive surfaces 740 wherein the fourth selected abrasive surface 740 comprises a plurality of micropillars having micropillar orientations at a fourth angle relative to a portion of a surface of blunt-tip membrane removing forceps 700. In one or more embodiments, a surgeon may maneuver a portion of a fourth selected abrasive surface 740 across a portion of a membrane, e.g., to perform a fourth attempt to raise a portion of the membrane. If the fourth attempt to raise a portion of the membrane is unsuccessful, then the surgeon may select an abrasive surface 740 having a plurality of micropillars wherein the plurality of micropillars have micropillar orientations at an angle greater than the fourth angle relative to a portion of a surface of blunt-tip membrane removing forceps 700, e.g., by manipulating an orientation of blunt-tip membrane removing forceps 700. Illustratively, a surgeon may select a fifth selected abrasive surface 740 of a plurality of abrasive surfaces 740 wherein the fifth selected abrasive surface 740 is configured to minimize an amount of trauma to the underlying tissue, e.g., a surgeon may select a fifth selected abrasive surface 740 of a plurality of abrasive surfaces 740 wherein the fifth selected abrasive surface 740 comprises a plurality of micropillars having micropillar orientations at a fifth angle relative to a portion of a surface of blunt-tip membrane removing forceps 700. In one or more embodiments, a surgeon may maneuver a portion of a fifth selected abrasive surface 740 across a portion of a membrane, e.g., to perform a fifth attempt to raise a portion of the membrane.

Illustratively, each forceps jaw 710 of a plurality of forceps jaws 710 may comprise a forceps jaw distal end 711 and a forceps jaw proximal end 712. In one or more embodiments, a first forceps jaw distal end 711 and a second forceps jaw distal end 711 may be separated by a maximum forceps jaw separation distance 715. Illustratively, a maximum forceps jaw separation distance 715 may be in a range of 0.005 to 0.08 inches, e.g., a maximum forceps jaw separation distance 715 may be 0.04 inches. In one or more embodiments, a maximum forceps jaw separation distance 715 may be less than 0.005 inches or greater than 0.08 inches. Illustratively, blunt-tip membrane removing forceps 700 may be configured to separate a first tissue from a surface of a second tissue without damaging the second tissue. For example, blunt-tip membrane removing forceps 700 may be configured to separate a first tissue having a convex surface geometry from a second tissue having a convex surface geometry without damaging the second tissue. In one or more embodiments, the first tissue may comprise an internal limiting membrane 650 and the second tissue may comprise a retinal tissue 670. Illustratively, a maximum forceps jaw separation distance 715 may be in a range of 200.0 to 600.0 times greater than an average thickness of the first tissue, e.g., a maximum forceps jaw separation distance 715 may be 291.0 times greater than an average thickness of the first tissue. In one or more embodiments, a maximum forceps jaw separation distance 715 may be less than 200.0 times or greater than 600.0 times greater than an average thickness of the first tissue. Illustratively, a maximum forceps jaw separation distance 715 may be in a range of 200.0 to 600.0 times greater than an average thickness of internal limiting membrane 650, e.g., a maximum forceps jaw separation distance 715 may be 291.0 times greater than an average thickness of internal limiting membrane 650. In one or more embodiments, a maximum forceps jaw separation distance 715 may be less than 200.0 times or greater than 600.0 times greater than an average thickness of internal limiting membrane 650.

Illustratively, third contour angle 720 may comprise any angle less than 90.0 degrees, e.g., third contour angle 720 may comprise any angle in a range of 60.0 to 80.0 degrees. In one or more embodiments, third contour angle 720 may comprise an angle less than 60.0 degrees or greater than 80.0 degrees. Illustratively, third contour angle 720 may comprise a 70.0 degree angle. In one or more embodiments, fourth contour angle 730 may comprise any angle greater than 90.0 degrees, e.g., fourth contour angle 730 may comprise any angle in a range of 95.0 to 120.0 degrees. Illustratively, fourth contour angle 730 may comprise an angle less than 95.0 degrees or greater than 120.0 degrees. In one or more embodiments, fourth contour angle 730 may comprise a 110.0 degree angle.

In one or more embodiments, forceps jaws 710 may be configured to close at forceps jaws distal ends 711 as outer hypodermic tube 170 is gradually actuated over forceps jaws proximal ends 712. Illustratively, an extension of outer hypodermic tube 170 relative to surgical blank 180 may be configured to decrease a distance between a first forceps jaw distal end 711 and a second forceps jaw distal end 711. In one or more embodiments, an extension of outer hypodermic tube 170 over a first forceps jaw proximal end 712 and a second forceps jaw proximal end 712 may be configured to cause the first forceps jaw distal end 711 and the second forceps jaw distal end 711 to contact before any other portion of the first forceps jaw 710 contacts any other portion of the second forceps jaw 710.

FIGS. 8A, 8B, 8C, 8D, 8E, and 8F are schematic diagrams illustrating a gradual closing of a blunt-tip membrane removing forceps 800. FIG. 8A illustrates a top view and FIG. 8B illustrates a front view of an open blunt-tip membrane removing forceps 800. In one or more embodiments, blunt-tip membrane removing forceps 700 may comprise an open blunt-tip membrane removing forceps 800, e.g., when a first forceps jaw distal end 711 is separated from a second forceps jaw distal end 711 by maximum forceps jaw separation distance 715. Illustratively, blunt-tip membrane removing forceps 700 may comprise an open blunt-tip membrane removing forceps 800, e.g., when outer hypodermic tube 170 is fully retracted relative to forceps jaws proximal ends 712. Illustratively, blunt-tip membrane removing forceps 700 may comprise an open blunt-tip membrane removing forceps 800, e.g., when handle 110 is fully decompressed.

FIG. 8C illustrates a top view and FIG. 8D illustrates a front view of a partially closed blunt-tip membrane removing forceps 810. In one or more embodiments, a compression of handle 110 may be configured to gradually close a blunt-tip membrane removing forceps 700, e.g., from an open blunt-tip membrane removing forceps 800 to a partially closed blunt-tip membrane removing forceps 810. Illustratively, a compression of handle 110 may be configured to extend outer hypodermic tube 170 relative to surgical blank 180, e.g., a compression of handle 110 may be configured to extend outer hypodermic tube distal end 171 over forceps jaws proximal ends 712. In one or more embodiments, a compression of handle 110 may be configured to decrease a distance between a first forceps jaw distal end 711 and a second forceps jaw distal end 711, e.g., a first forceps jaw distal end 711 and a second forceps jaw distal end 711 may be separated by a distance less than maximum forceps jaw separation distance 715 when blunt-tip membrane removing forceps 700 comprises a partially closed blunt-tip membrane removing forceps 810.

FIG. 8E illustrates a top view and FIG. 8F illustrates a front view of a fully closed blunt-tip membrane removing forceps 820. Illustratively, a compression of handle 110 may be configured to gradually close a blunt-tip membrane removing forceps 700, e.g., from a partially closed blunt-tip membrane removing forceps 810 to a fully closed blunt-tip membrane removing forceps 820. In one or more embodiments, a compression of handle 110 may be configured to extend outer hypodermic tube 170 relative to surgical blank 180, e.g., a compression of handle 110 may be configured to extend outer hypodermic tube distal end 171 over forceps jaws proximal ends 712. Illustratively, an extension of outer hypodermic tube 170 over forceps jaws proximal ends 712 may be configured to close forceps jaws 710 wherein forceps jaws 710 initially contact at forceps jaws distal ends 711. In one or more embodiments, a first forceps jaw distal end 711 may be adjacent to a second forceps jaw distal end 711, e.g., when blunt-tip membrane removing forceps 700 comprises a fully closed blunt-tip membrane removing forceps 820.

Figure 9C:
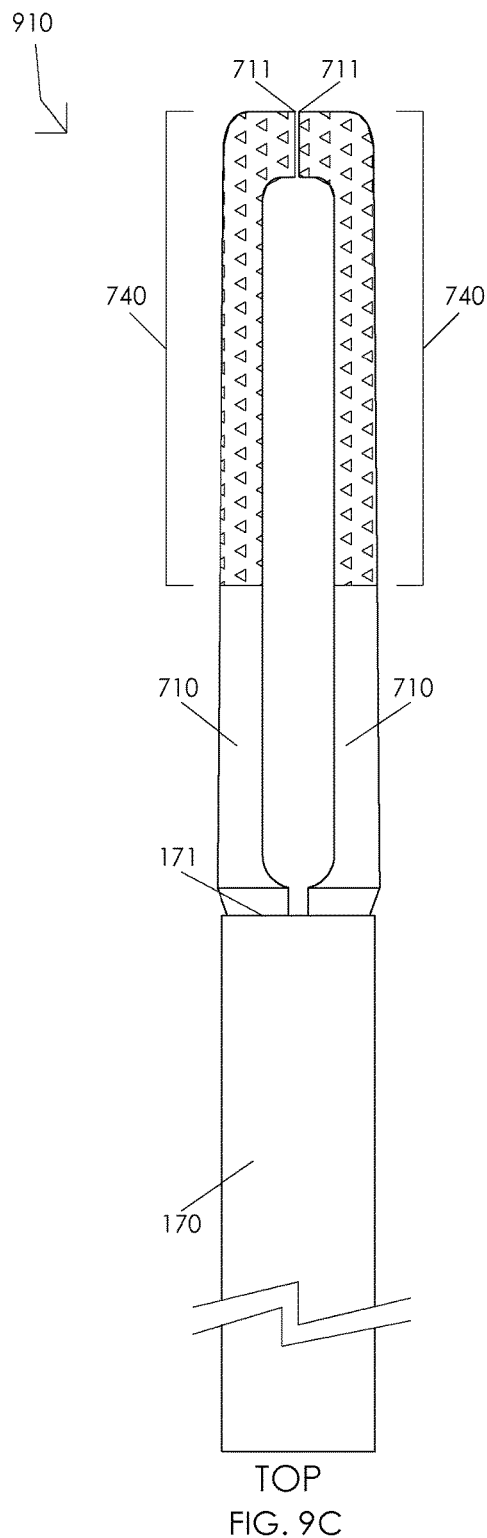

FIGS. 9A, 9B, 9C, 9D, 9E, and 9F are schematic diagrams illustrating a gradual opening of a blunt-tip membrane removing forceps 700. FIG. 9A illustrates a top view and FIG. 9B illustrates a front view of a closed blunt-tip membrane removing forceps 900. In one or more embodiments, blunt-tip membrane removing forceps 700 may comprise a closed blunt-tip membrane removing forceps 900, e.g., when a first forceps jaw distal end 711 is adjacent to a second forceps jaw distal end 711. Illustratively, blunt-tip membrane removing forceps 700 may comprise a closed blunt-tip membrane removing forceps 900, e.g., when outer hypodermic tube 170 is fully extended over forceps jaws proximal ends 712. Illustratively, blunt-tip membrane removing forceps 700 may comprise a closed blunt-tip membrane removing forceps 900, e.g., when handle 110 is fully compressed.

Figure 9D:
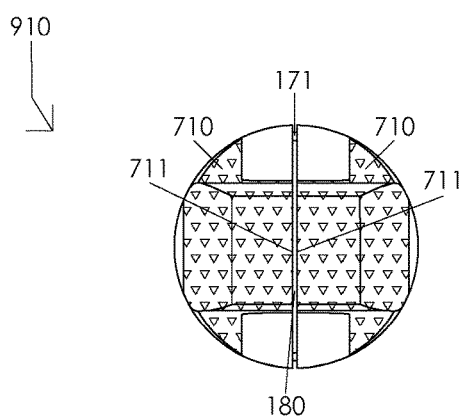

FIG. 9C illustrates a top view and FIG. 9D illustrates a front view of a partially open blunt-tip membrane removing forceps 910. In one or more embodiments, a decompression of handle 110 may be configured to gradually open a blunt-tip membrane removing forceps 700, e.g., from a closed blunt-tip membrane removing forceps 900 to a partially open blunt-tip membrane removing forceps 910. Illustratively, a decompression of handle 110 may be configured to retract outer hypodermic tube 170 relative to surgical blank 180, e.g., a decompression of handle 110 may be configured to retract outer hypodermic tube distal end 171 relative to forceps jaws proximal ends 712. In one or more embodiments, a decompression of handle 110 may be configured to gradually separate forceps jaws 710. Illustratively, a decompression of handle 110 may be configured to separate forceps jaws 710 wherein forceps jaws distal ends 711 are the last portions of forceps jaws 710 to separate.

FIG. 9E illustrates a top view and FIG. 9F illustrates a front view of a fully open blunt-tip membrane removing forceps 920. Illustratively, a decompression of handle 110 may be configured to gradually open a blunt-tip membrane removing forceps 700, e.g., from a partially open blunt-tip membrane removing forceps 910 to a fully open blunt-tip membrane removing forceps 920. In one or more embodiments, a decompression of handle 110 may be configured to retract outer hypodermic tube 170 relative to surgical blank 180, e.g., a decompression of handle 110 may be configured to retract outer hypodermic tube distal end 171 relative to forceps jaws proximal ends 712. Illustratively, a decompression of handle 110 may be configured to gradually separate forceps jaws 710. In one or more embodiments, a first forceps jaw distal end 711 and a second forceps jaw distal end 711 may be separated by maximum forceps jaw separation distance 715, e.g., when blunt-tip membrane removing forceps 700 comprises a fully open blunt-tip membrane removing forceps 920.

Figure 10A:
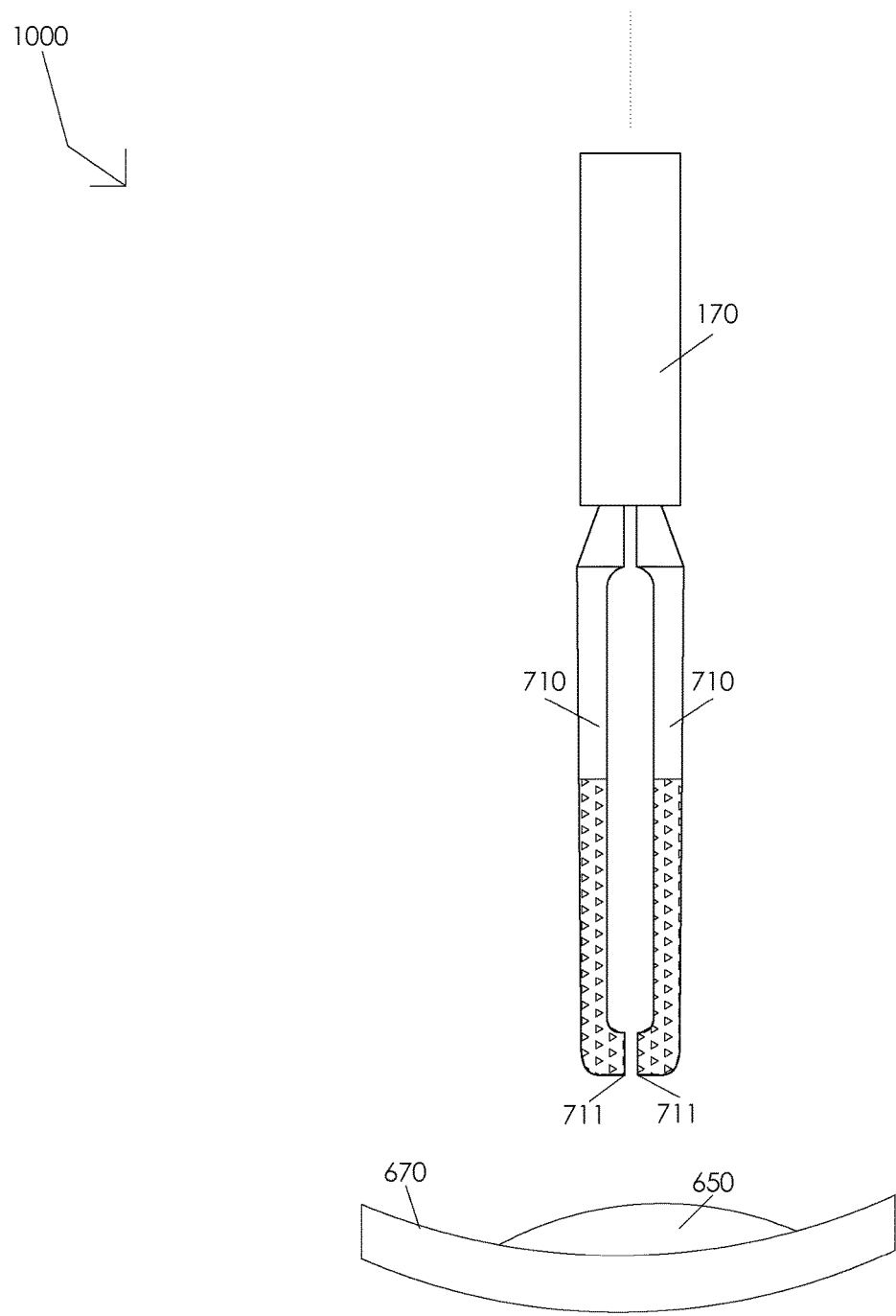
FIGS. 10A, 10B, 10C, 10D, and 10E are schematic diagrams illustrating a membrane removal.

FIGS. 10A, 10B, 10C, 10D, and 10E are schematic diagrams illustrating a membrane removal. FIG. 10A illustrates an attached membrane 1000. Illustratively, an attached membrane 1000 may comprise an internal limiting membrane 650 attached to a retinal tissue 670. In one or more embodiments, a surgeon may separate internal limiting membrane 650 from retinal tissue 670 by grasping internal limiting membrane 650 with forceps jaws 710, e.g., without damaging retinal tissue 670. Illustratively, a surgeon may manipulate handle 110 to approach retinal tissue 670 with blunt-tip membrane removing forceps 700, e.g., when blunt-tip membrane removing forceps 700 comprises an open blunt-tip membrane removing forceps 800. For example, a surgeon may gradually move forceps jaws distal ends 711 closer to retinal tissue 670 until forceps jaws distal ends 711 contact internal limiting membrane 650. In one or more embodiments, a compression of handle 110, e.g., by a surgeon, may be configured to extend outer hypodermic tube 170 over forceps jaws proximal ends 712. Illustratively, a surgeon may grasp internal limiting membrane 650 with forceps jaws distal ends 711 and no other portion of forceps jaws 710, e.g., to minimize trauma to an underlying retinal tissue 670.

Figure 10B:
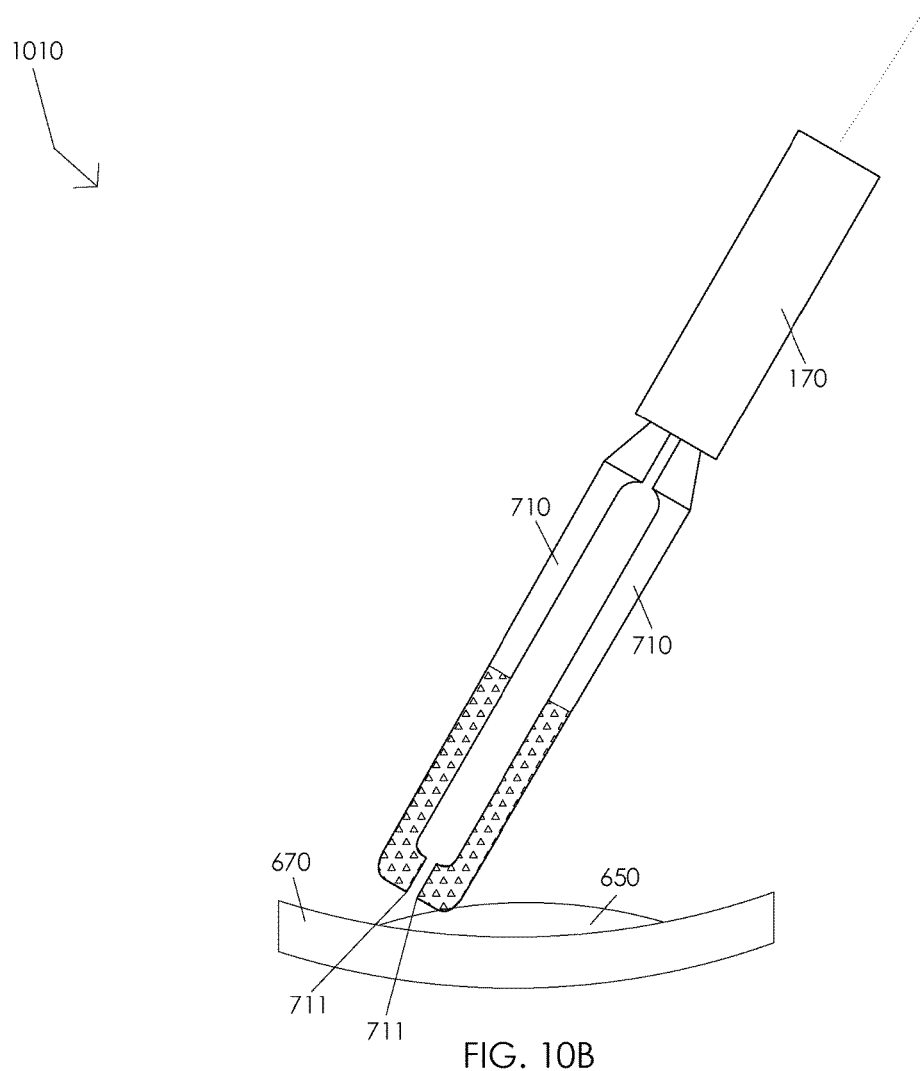

FIG. 10B illustrates a membrane grazing 1010. In one or more embodiments, a membrane grazing 1010 may be configured to raise a portion of a membrane, e.g., a membrane grazing 1010 may be configured to raise a portion of internal limiting membrane 650. Illustratively, a membrane grazing 1010 may comprise a contact between abrasive surface 740 and an internal limiting membrane 650. In one or more embodiments, abrasive surface 740 may be configured to grasp a portion of a membrane, e.g., internal limiting membrane 650. Illustratively, abrasive surface 740 may be configured to grasp and raise a portion of a membrane, e.g., internal limiting membrane 650. In one or more embodiments, abrasive surface 740 may be configured to grasp a portion of internal limiting membrane 650 and separate the portion of internal limiting membrane 650 from a portion of retinal tissue 670. Illustratively, a surgeon may maneuver a portion of abrasive surface 740 across a portion of a membrane, e.g., a surgeon may maneuver a portion of abrasive surface 740 across a portion of internal limiting membrane 650. In one or more embodiments, as a surgeon maneuvers a portion of abrasive surface 740 across a portion of internal limiting membrane 650, the surgeon may graze the portion of internal limiting membrane 650, e.g., by contacting the portion of internal limiting membrane 650 with abrasive surface 740. Illustratively, a contact between abrasive surface 740 and a portion of internal limiting membrane 650 may be configured to grasp the portion of internal limiting membrane 650. In one or more embodiments, a contact between abrasive surface 740 and a portion of internal limiting membrane 650 may be configured to grasp and raise the portion of internal limiting membrane 650. Illustratively, a surgeon may graze a portion of internal limiting membrane 650, e.g., by contacting abrasive surface 740 and a portion of internal limiting membrane 650 to grasp the portion of internal limiting membrane 650 and then actuating abrasive surface 740 relative to internal limiting membrane 650 to raise the portion of internal limiting membrane 650.

In one or more embodiments, a portion of forceps jaws distal ends 711 may comprise an abrasive surface 740, e.g., a portion of a first forceps jaw distal end 711 may comprise a first abrasive surface 740 and a portion of a second forceps jaw distal end 711 may comprise a second abrasive surface 740. Illustratively, a contact between a portion of a forceps jaw distal end 711 and a portion of a membrane may be configured to grasp the portion of the membrane. In one or more embodiments, a contact between a portion of a forceps jaw distal end 711 and a portion of internal limiting membrane 650 may be configured to grasp the portion of internal limiting membrane 650. Illustratively, a surgeon may contact a portion of internal limiting membrane 650 with forceps jaws distal ends 711, e.g., when blunt-tip membrane removing forceps 700 comprises a fully closed blunt-tip membrane removing forceps 820. In one or more embodiments, a contact between forceps jaws distal ends 711 and a portion of internal limiting membrane 650 when blunt-tip membrane removing forceps 700 comprises a fully closed blunt-tip membrane removing forceps 820 may be configured to grasp the portion of internal limiting membrane 650. Illustratively, after contacting a portion of internal limiting membrane 650 with forceps jaws distal ends 711 when blunt-tip membrane removing forceps 700 comprises a fully closed blunt-tip membrane removing forceps 820, a surgeon may decompress handle 110. In one or more embodiments, a decompression of handle 110 may be configured to gradually separate forceps jaws distal ends 711. Illustratively, a gradual separation of forceps jaws distal ends 711 may be configured to raise a portion of internal limiting membrane 650. In one or more embodiments, a surgeon may perform a membrane grazing 1010 by compressing handle 110 wherein blunt-tip membrane removing forceps 700 comprises a fully closed blunt-tip membrane removing forceps 820. Illustratively, the surgeon may then contact a portion of a membrane, e.g., an internal limiting membrane 650, with forceps jaws distal ends 711. In one or more embodiments, the surgeon may then decompress handle 110 to separate forceps jaws distal ends 711 while forceps jaws distal ends 711 contact the portion of the membrane. Illustratively, a separation of forceps jaws distal ends 711 while forceps jaws distal ends 711 contact the portion of the membrane may be configured to raise the portion of the membrane. For example, a separation of forceps jaws distal ends 711 while forceps jaws distal ends 711 contact a portion of an internal limiting membrane 650 may be configured to raise the portion of the internal limiting membrane 650.

Figure 10C:
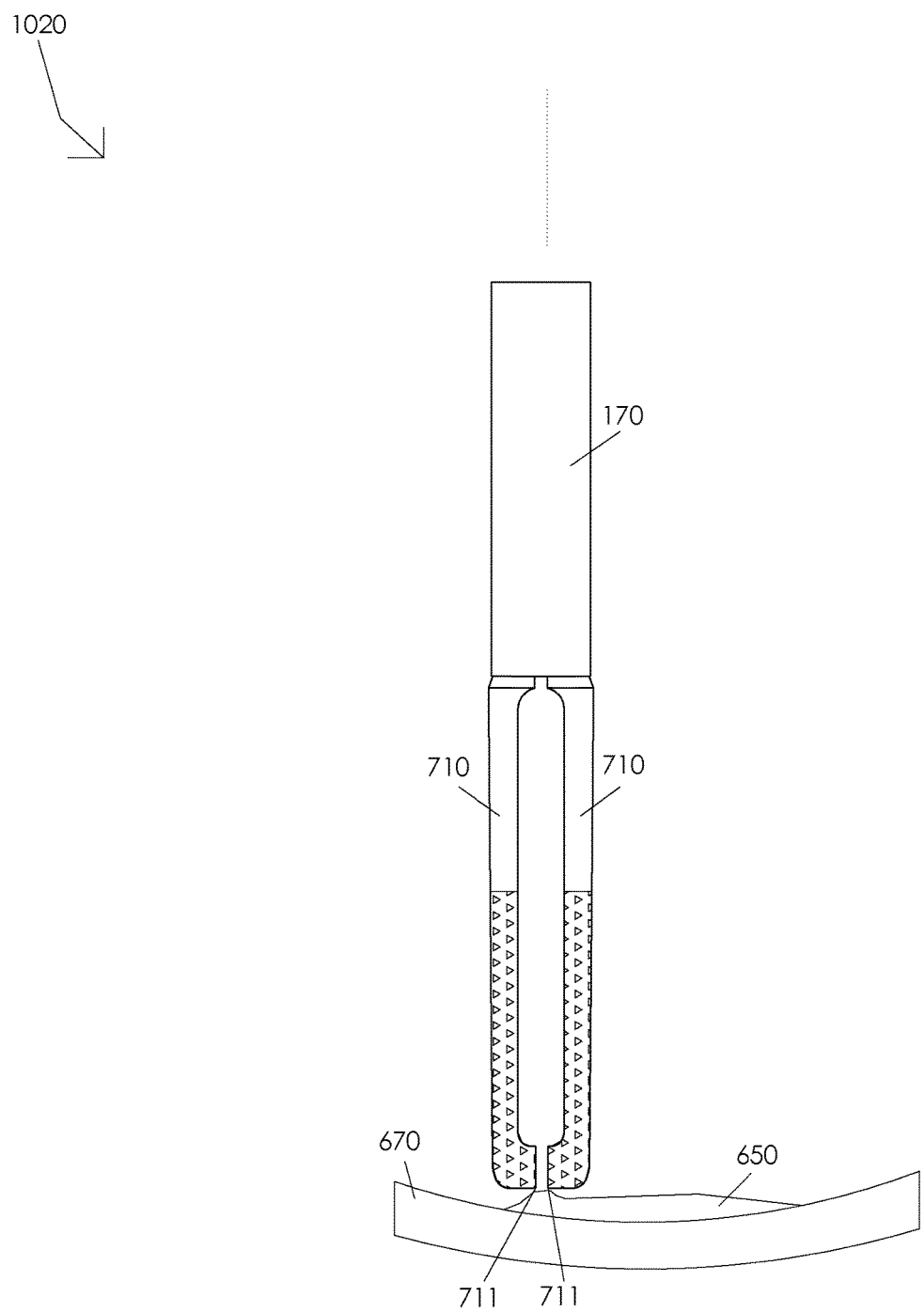

FIG. 10C illustrates a grasping of a raised portion of a membrane 1020. Illustratively, a surgeon may grasp a portion of a membrane, e.g., a raised portion of internal limiting membrane 650, with blunt-tip membrane removing forceps 700 by compressing handle 110. In one or more embodiments, a surgeon may grasp a portion of a membrane, e.g., a raised portion of internal limiting membrane 650, by disposing the portion of the membrane in between forceps jaws 710 and compressing handle 110. Illustratively, a surgeon may raise a portion of internal limiting membrane 650, e.g., by performing a membrane grazing 1010. In one or more embodiments, a surgeon may grasp the raised portion of internal limiting membrane 650, e.g., by maneuvering forceps jaws 710 wherein the raised portion of internal limiting membrane 650 is disposed between forceps jaws distal ends 711. Illustratively, a surgeon may grasp a raised portion of internal limiting membrane 650 disposed between forceps jaws distal ends 711, e.g., by compressing handle 110.

Figure 10D:
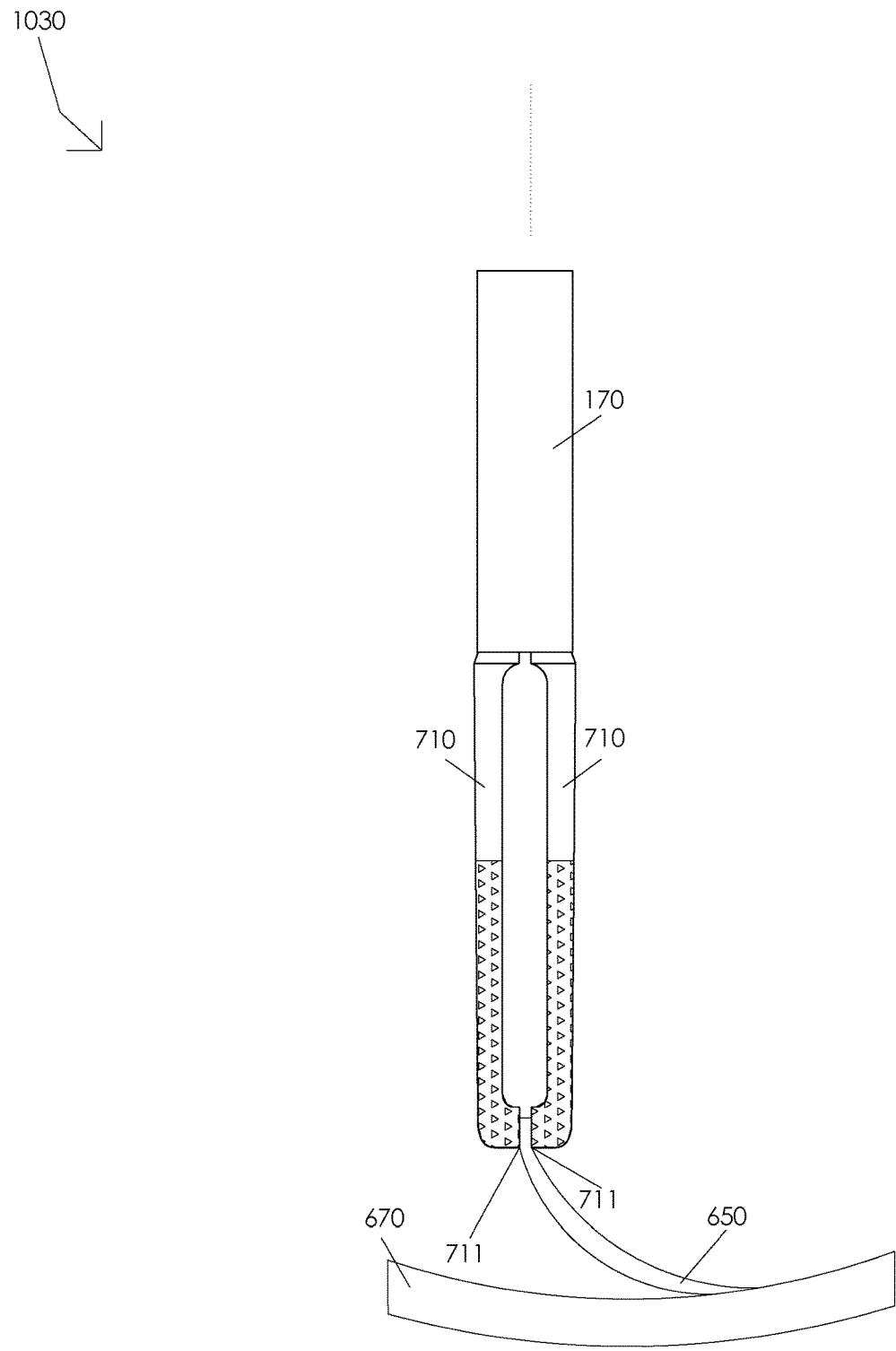

FIG. 10D illustrates a partially peeled membrane 1030. Illustratively, a partially peeled membrane 1030 may comprise an internal limiting membrane 650 partially separated from a retinal tissue 670. In one or more embodiments, a surgeon may raise a portion of a membrane, e.g., an internal limiting membrane 650, by performing a membrane grazing 1010. Illustratively, a surgeon may grasp a raised portion of a membrane, e.g., an internal limiting membrane 650, by performing a grasping of a raised portion of a membrane 1020. In one or more embodiments, a surgeon may peel a membrane apart from an underlying tissue by grasping the membrane with blunt-tip membrane removing forceps 700 and pulling the membrane apart from the underlying tissue. Illustratively, a surgeon may peel an internal limiting membrane 650 apart from an underlying retinal tissue 670 by grasping internal limiting membrane 650 with blunt-tip membrane removing forceps 700 and pulling internal limiting membrane 650 apart from retinal tissue 670. In one or more embodiments, a surgeon may peel a membrane apart from an underlying tissue by grasping the membrane with blunt-tip membrane removing forceps 700 and pulling the membrane apart from the underlying tissue until the membrane comprises a partially peeled membrane 1030. Illustratively, a surgeon may peel an internal limiting membrane 650 apart from an underlying retinal tissue 670 by grasping internal limiting membrane 650 with blunt-tip membrane removing forceps 700 and pulling internal limiting membrane 650 apart from retinal tissue 670 until internal limiting membrane 650 comprises a partially peeled membrane 1030.

Figure 10E:
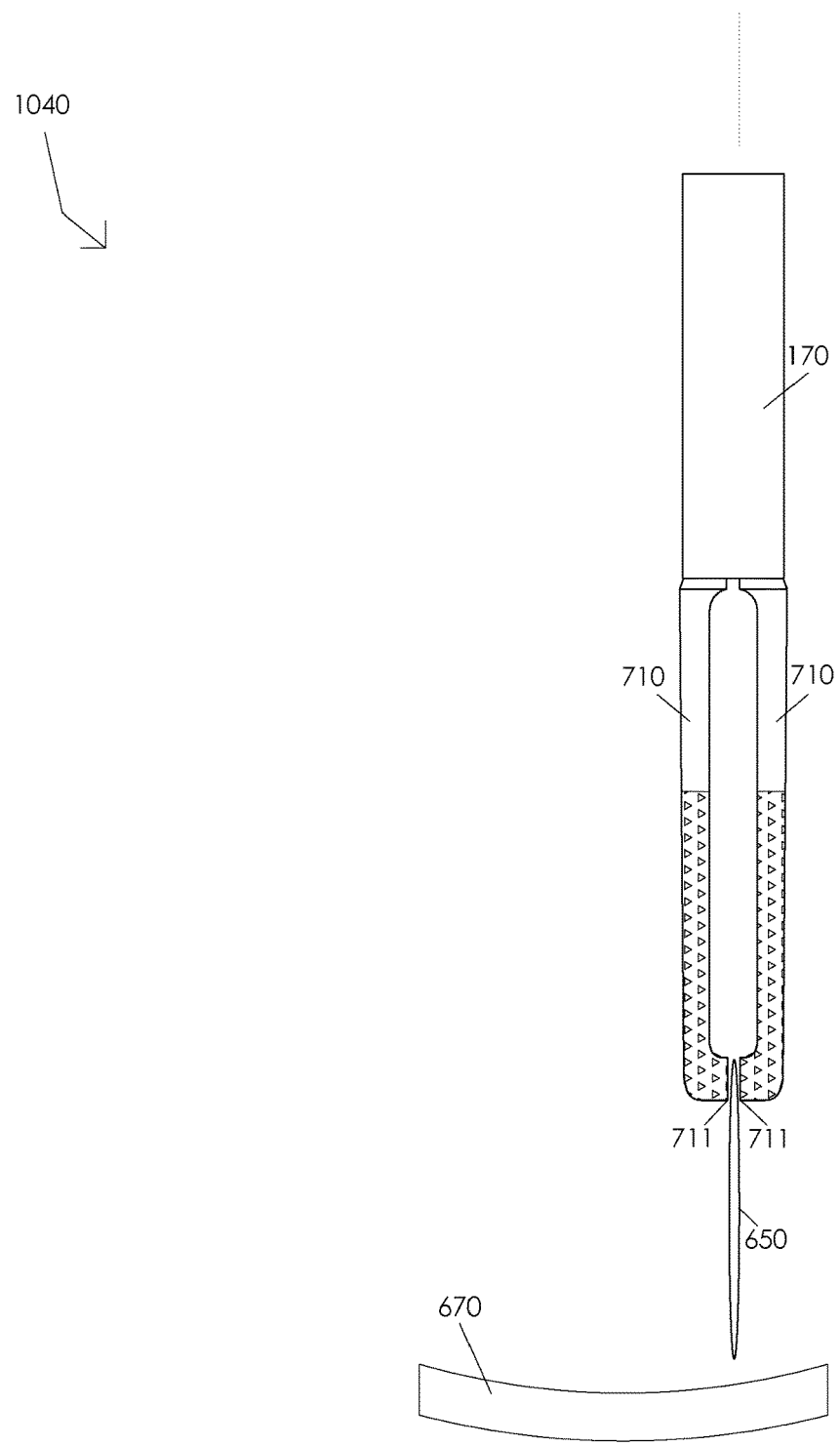

FIG. 10E illustrates a fully peeled membrane 1040. Illustratively, a fully peeled membrane 1040 may comprise an internal limiting membrane 650 completely separated from a retinal tissue 670. In one or more embodiments, a surgeon may peel a membrane apart from an underlying tissue by grasping the membrane with blunt-tip membrane removing forceps 700 and pulling the membrane apart from the underlying tissue until the membrane comprises a fully peeled membrane 1040. Illustratively, a surgeon may continue to peel a partially peeled membrane 1030 apart from an underlying tissue until the membrane comprises a fully peeled membrane 1040. In one or more embodiments, a surgeon may peel an internal limiting membrane 650 apart from an underlying retinal tissue 670 by grasping internal limiting membrane 650 with blunt-tip membrane removing forceps 700 and pulling internal limiting membrane 650 apart from retinal tissue 670 until internal limiting membrane 650 comprises a fully peeled membrane 1040. Illustratively, a surgeon may continue to peel a partially peeled membrane 1030 apart from retinal tissue 670 until internal limiting membrane 650 comprises a fully peeled membrane 1040.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a surgical instrument, the teachings of the present invention are equally suitable to any systems where the functionality may be employed. Therefore, it is the object of the appended claims to cover all such variations and modifications as come within the true spirit and scope of the invention.

What is claimed is:

1. An ophthalmic surgical forceps comprising:
   a handle having a handle distal end and a handle proximal end;
   a surgical blank having a surgical blank distal end and a surgical blank proximal end, the surgical blank at least partially disposed in the handle wherein the surgical blank has dimensions configured for performing ophthalmic surgical procedures;
   a first abrasive surface of the surgical blank, the first abrasive surface configured to raise a portion of a membrane wherein the first abrasive surface is disposed in a first location on the surgical blank;
   a first plurality of micropillars of the first abrasive surface wherein the first plurality of micropillars have micropillar diameters in a range of 5.0 to 15.0 micrometers wherein the first plurality of micropillars are manufactured by modifying the blank in a repeated geometric pattern;
   a second abrasive surface of the surgical blank, the second abrasive surface configured to raise the portion of the membrane wherein the second abrasive surface is disposed in a second location on the surgical blank; and
   a second plurality of micropillars of the second abrasive surface wherein the second plurality of micropillars have micropillar diameters in a range of 5.0 to 15.0 micrometers wherein the second plurality of micropillars are manufactured by modifying the blank in the repeated geometric pattern.

2. The ophthalmic surgical forceps of claim 1 wherein the first plurality of micropillars have micropillar heights in a range of 0.25 to 2.25 micrometers.

3. The ophthalmic surgical forceps of claim 2 wherein the second plurality of micropillars have micropillar heights in a range of 0.25 to 2.25 micrometers.

4. The ophthalmic surgical forceps of claim 1 wherein the first plurality of micropillars have micropillar heights greater than 3.0 micrometers.

5. The ophthalmic surgical forceps of claim 4 wherein the second plurality of micropillars have micropillar heights greater than 3.0 micrometers.

6. The ophthalmic surgical forceps of claim 1 wherein the first plurality of micropillars are oriented at angles in a range of 60.0 to 89.0 degrees relative to a first surface of the surgical blank.

7. The ophthalmic surgical forceps of claim 1 wherein the second plurality of micropillars are oriented at angles in a range of 60.0 to 89.0 degrees relative to a second surface of the surgical blank.

8. The ophthalmic surgical forceps of claim 1 wherein the first plurality of micropillars have micropillar orientations normal to a first surface of the surgical blank.

9. The ophthalmic surgical forceps of claim 8 wherein the second plurality of micropillars have micropillar orientations normal to a second surface of the surgical blank.

10. The ophthalmic surgical forceps of claim 1 wherein the membrane is an internal limiting membrane.

11. The ophthalmic surgical forceps of claim 1 wherein the surgical blank is manufactured from metal.

12. The ophthalmic surgical forceps of claim 1 wherein the first plurality of micropillars are manufactured by modifying the surgical blank in the repeated geometric pattern by an electric discharge machine.

13. The ophthalmic surgical forceps of claim 1 wherein the first plurality of micropillars are manufactured by modifying the surgical blank in the repeated geometric pattern by a laser.

14. The ophthalmic surgical forceps of claim 1 further comprising:
    a third abrasive surface of the surgical blank, the third abrasive surface configured to raise the portion of the membrane wherein the third abrasive surface is disposed in a third location on the surgical blank.

15. The ophthalmic surgical forceps of claim 14 further comprising:
    a third plurality of micropillars of the third abrasive surface.

16. The ophthalmic surgical forceps of claim 15 wherein the third plurality of micropillars have micropillar diameters in a range of 5.0 to 15.0 micrometers.

17. The ophthalmic surgical forceps of claim 15 wherein the third plurality of micropillars are manufactured by modifying the surgical blank in the repeated geometric pattern.

18. The ophthalmic surgical forceps of claim 15 wherein the third plurality of micropillars have micropillar heights in a range of 0.25 to 2.25 micrometers.

19. The ophthalmic surgical forceps of claim 15 wherein the third plurality of micropillars have micropillar heights greater than 3.0 micrometers.

20. The ophthalmic surgical forceps of claim 15 wherein the surgical blank is manufactured from metal.

* * * * *